United States Patent
Dong et al.

(10) Patent No.: US 12,326,453 B2
(45) Date of Patent: *Jun. 10, 2025

(54) COMPOSITIONS AND METHODS FOR ACTIVE SURVEILLANCE OF PROSTATE CANCER

(71) Applicant: OPKO Diagnostics, LLC, Woburn, MA (US)

(72) Inventors: Yan Dong, Medford, MA (US); Andrew J. Vickers, Brooklyn, NY (US); Daniel Sjoberg, New York, NY (US); Peter T. Scardino, New York, NY (US); Hans Lilja, New York, NY (US)

(73) Assignee: OPKO Diagnostics, LLC, Woburn, MA (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/143,345

(22) Filed: Apr. 29, 2016

(65) Prior Publication Data

US 2017/0089904 A1    Mar. 30, 2017

Related U.S. Application Data

(63) Continuation-in-part of application No. 14/671,355, filed on Mar. 27, 2015, now Pat. No. 11,761,962.

(60) Provisional application No. 62/154,616, filed on Apr. 29, 2015, provisional application No. 61/972,099, filed on Mar. 28, 2014.

(51) Int. Cl.
| | |
|---|---|
| G01N 33/53 | (2006.01) |
| G01N 33/574 | (2006.01) |
| G06N 7/01 | (2023.01) |
| G16B 20/00 | (2019.01) |
| G16B 40/00 | (2019.01) |
| G16H 50/20 | (2018.01) |

(52) U.S. Cl.
CPC ......... *G01N 33/57434* (2013.01); *G06N 7/01* (2023.01); *G16B 20/00* (2019.02); *G16B 40/00* (2019.02); *G16H 50/20* (2018.01); *G01N 2333/96455* (2013.01)

(58) Field of Classification Search
CPC ... G01N 33/57434; G01N 2333/96455; G06N 7/005; G16B 20/00; G16B 40/00; G16H 50/20
See application file for complete search history.

(56) References Cited

U.S. PATENT DOCUMENTS

| | | | |
|---|---|---|---|
| 5,516,639 A | 5/1996 | Tindall et al. |
| 5,585,069 A | 12/1996 | Zanzucchi et al. |
| 5,614,372 A | 3/1997 | Lilja et al. |
| 5,638,828 A | 6/1997 | Lauks et al. |
| 5,672,480 A | 9/1997 | Dowell et al. |
| 5,840,501 A | 11/1998 | Allard et al. |
| 5,939,533 A | 8/1999 | Lilja et al. |
| 5,945,289 A | 8/1999 | Lehrer |
| 6,143,509 A | 11/2000 | Dowell et al. |
| 6,207,369 B1 | 3/2001 | Wohlstadter et al. |
| 6,444,425 B1 | 9/2002 | Reed et al. |
| 6,713,271 B1 | 3/2004 | Feistel |
| 6,929,918 B1 | 8/2005 | Charrier et al. |
| 7,211,397 B2 | 5/2007 | Mikolajczy et al. |
| 7,258,837 B2 | 8/2007 | Yager et al. |
| 7,605,003 B2 | 10/2009 | Chan et al. |
| 7,736,890 B2 | 6/2010 | Babak et al. |
| 7,872,104 B2 | 1/2011 | Pettersson et al. |
| 7,951,529 B2 | 5/2011 | Li et al. |
| 8,030,057 B2 | 10/2011 | Linder et al. |
| 8,173,433 B2 | 5/2012 | Folkman et al. |
| 8,192,931 B2 | 6/2012 | Fradet et al. |
| 8,580,569 B2 | 11/2013 | Linder et al. |
| 8,591,829 B2 | 11/2013 | Taylor et al. |
| 8,663,600 B2 | 3/2014 | Ulmert |
| 8,765,062 B2 | 7/2014 | Linder et al. |
| 8,932,523 B2 | 1/2015 | Linder et al. |
| 9,182,400 B2 | 11/2015 | Mattsson et al. |
| 9,345,782 B2 | 5/2016 | Strand et al. |
| 9,377,463 B2 | 6/2016 | Krek et al. |
| 9,561,506 B2 | 2/2017 | Taylor et al. |
| 9,643,182 B2 | 5/2017 | Linder et al. |
| 9,672,329 B2 | 6/2017 | Vickers et al. |
| 9,682,376 B2 | 6/2017 | Linder et al. |
| 9,770,715 B2 | 9/2017 | Steinmiller et al. |
| 9,827,563 B2 | 11/2017 | Steinmiller et al. |
| 9,827,564 B2 | 11/2017 | Steinmiller et al. |
| 9,878,324 B2 | 1/2018 | Taylor et al. |
| 10,775,369 B2 | 9/2020 | Linder et al. |

(Continued)

FOREIGN PATENT DOCUMENTS

| | | |
|---|---|---|
| CN | 1973778 A | 6/2007 |
| CN | 101329343 A | 12/2008 |

(Continued)

OTHER PUBLICATIONS

Vickers et al. (Journal of Clinical Oncology, 2010 vol 28 No 15 pp. 2493-2498).*
Hernandez et al (BJU Int. Mar. 2009 ; 103(5): 609-614).*
Vickers et al. (Cancer Epidemiol Biomarkers Prev 2011;20:255-261).*
Hirama et al. (J.Cancer Res Clin Oncol 2014; published on-line in 2013; 140:257-263.*

(Continued)

*Primary Examiner* — Carmencita M Belei

(74) *Attorney, Agent, or Firm* — Wolf, Greenfield & Sacks, P.C.

(57) ABSTRACT

Aspects of the disclosure relate to improved methods and systems for active surveillance of subject having non-aggressive prostate cancer.

3 Claims, 19 Drawing Sheets

(56) References Cited

U.S. PATENT DOCUMENTS

| | | | |
|---|---|---|---|
| 11,761,962 B2 * | 9/2023 | Linder | G16B 40/00 |
| | | | 702/19 |
| 11,921,115 B2 | 3/2024 | Linder et al. | |
| 12,131,802 B2 | 10/2024 | Vickers et al. | |
| 2003/0235816 A1 | 12/2003 | Slawin et al. | |
| 2004/0101914 A1 | 5/2004 | Pettersson et al. | |
| 2005/0118061 A1 | 6/2005 | Mototsu et al. | |
| 2005/0272052 A1 | 12/2005 | Shekar et al. | |
| 2005/0282199 A1 | 12/2005 | Slawin et al. | |
| 2006/0154276 A1 | 7/2006 | Lois et al. | |
| 2006/0269971 A1 | 11/2006 | Diamandis | |
| 2007/0065954 A1 | 3/2007 | Taya et al. | |
| 2007/0099219 A1 | 5/2007 | Teverovskiy et al. | |
| 2009/0035773 A1 | 2/2009 | Harvey et al. | |
| 2009/0087860 A1 | 4/2009 | Todd et al. | |
| 2009/0127454 A1 | 5/2009 | Ritchie et al. | |
| 2009/0226912 A1 | 9/2009 | Xu et al. | |
| 2010/0100334 A1 | 4/2010 | Otvos | |
| 2010/0158756 A1 | 6/2010 | Linder et al. | |
| 2010/0168621 A1 | 7/2010 | Neville | |
| 2011/0039284 A1 | 2/2011 | Breit et al. | |
| 2011/0229489 A1 | 9/2011 | Pons et al. | |
| 2011/0301863 A1 | 12/2011 | Auribault et al. | |
| 2012/0022793 A1 | 1/2012 | Barker et al. | |
| 2012/0122243 A1 | 5/2012 | Kamlage et al. | |
| 2012/0141376 A1 | 6/2012 | Einstein et al. | |
| 2012/0269701 A1 | 10/2012 | Linder et al. | |
| 2013/0157286 A1 | 6/2013 | Linder et al. | |
| 2013/0224209 A1 | 8/2013 | Wang et al. | |
| 2013/0273643 A1 * | 10/2013 | Vickers | G16H 10/40 |
| | | | 435/287.2 |
| 2014/0011861 A1 | 1/2014 | McClelland et al. | |
| 2014/0023565 A1 | 1/2014 | Taylor et al. | |
| 2014/0037716 A1 | 2/2014 | Nowill | |
| 2014/0038166 A1 | 2/2014 | Linder et al. | |
| 2014/0038167 A1 | 2/2014 | Linder et al. | |
| 2014/0038838 A1 | 2/2014 | Narain et al. | |
| 2014/0107180 A1 | 4/2014 | Macleod et al. | |
| 2014/0134603 A1 | 5/2014 | Sia et al. | |
| 2014/0227720 A1 | 8/2014 | Wilson et al. | |
| 2014/0234180 A1 | 8/2014 | Linder et al. | |
| 2015/0044666 A1 | 2/2015 | Jablonski et al. | |
| 2015/0086997 A1 | 3/2015 | Linder et al. | |
| 2015/0094221 A1 | 4/2015 | Gronberg et al. | |
| 2015/0233901 A1 | 8/2015 | Linder et al. | |
| 2015/0284804 A1 | 10/2015 | Gronberg et al. | |
| 2015/0317431 A1 | 11/2015 | Gronberg et al. | |
| 2015/0343443 A1 | 12/2015 | Linder et al. | |
| 2016/0025732 A1 * | 1/2016 | Linder | G16B 20/00 |
| | | | 702/19 |
| 2016/0268112 A1 | 9/2016 | Yip et al. | |
| 2016/0282349 A1 | 9/2016 | Linder et al. | |
| 2016/0305878 A1 | 10/2016 | Steinmiller et al. | |
| 2016/0305937 A1 | 10/2016 | Steinmiller et al. | |
| 2016/0305938 A1 | 10/2016 | Linder et al. | |
| 2016/0320394 A1 | 11/2016 | Dong et al. | |
| 2016/0369009 A1 | 12/2016 | Timmermand et al. | |
| 2017/0091379 A1 | 3/2017 | Vickers et al. | |
| 2017/0091380 A1 | 3/2017 | Vickers et al. | |
| 2017/0108501 A1 | 4/2017 | Gronberg | |
| 2017/0165661 A1 | 6/2017 | Taylor et al. | |
| 2017/0168060 A1 | 6/2017 | Vickers et al. | |
| 2017/0239656 A1 | 8/2017 | Linder et al. | |
| 2018/0085753 A1 | 3/2018 | Steinmiller et al. | |
| 2019/0072555 A1 | 3/2019 | Linder | |
| 2021/0208146 A1 | 7/2021 | Okrongly et al. | |
| 2024/0159758 A1 | 5/2024 | Linder et al. | |

FOREIGN PATENT DOCUMENTS

| | | | |
|---|---|---|---|
| CN | 101377500 A | 3/2009 | |
| CN | 102818892 A | 12/2012 | |
| EP | 0 635 575 A1 | 1/1995 | |
| JP | 2009-524008 A | 6/2009 | |
| JP | 2009-189695 A | 8/2009 | |
| JP | 2010-243406 A | 10/2010 | |
| TW | 200538734 A | 12/2005 | |
| WO | WO 97/06437 A1 | 2/1997 | |
| WO | WO 97/39351 A | 10/1997 | |
| WO | WO 99/45398 A1 | 9/1999 | |
| WO | WO 02/46448 A2 | 6/2002 | |
| WO | WO 2003/029427 A2 | 4/2003 | |
| WO | WO 03/100425 A1 | 12/2003 | |
| WO | WO 2005/056186 A1 | 6/2005 | |
| WO | WO 2010/127322 A1 | 11/2010 | |
| WO | WO 2011/027308 A1 | 3/2011 | |
| WO | WO 2011/027310 A1 | 3/2011 | |
| WO | WO 2012/029080 A | 3/2012 | |
| WO | WO2012129408 * | 9/2012 | G01N 33/53 |
| WO | WO 2013/012028 A1 | 1/2013 | |
| WO | WO 2013/134179 A2 | 9/2013 | |
| WO | WO 2013/172779 A2 | 11/2013 | |
| WO | WO 2014/079865 * | 4/2014 | |
| WO | WO 2014/079874 A1 | 5/2014 | |

OTHER PUBLICATIONS

Helbing et al (Cancer World, Jan./Feb. 2010, pp. 1-21.*
Vickers et al, MED Decis Making 2006;26:565-574.*
Nordstrom et al (European Urology 68, epub Aug. 2014, pp. 139-146.*
Office Action for Application No. FI 20125238 mailed Jan. 10, 2013.
International Search Report and Written Opinion for PCT/US2015/023096 mailed Jul. 6, 2015.
International Search Report and Written Opinion for PCT/US2016/029959 mailed Aug. 5, 2016.
Becker et al., Sensitive and specific immunodetection of human glandular kallikrein 2 in serum. Clin Chem. Feb. 2000;46(2):198-206.
Benchikh et al., A panel of kallikrein markers can predict outcome of prostate biopsy following clinical work-up: An independent validation study from the European Randomized Study of Prostate Cancer screening, France. BMC Cancer, 10:635 (2010).
Bryant et al., Predicting high-grade cancer at ten-core prostate biopsy using four kallikrein markers measured in blood in the ProtecT study. J Natl Cancer Inst. Apr. 11, 2015;107(7). pii: djv095. doi: 10.1093/jnci/djv095. Print Jul. 2015.
Carlsson et al., Predictive value of four kallikrein markers for pathologically insignificant compared with aggressive prostate cancer in radical prostatectomy specimens: results from the European randomized study of screening for prostate cancer section Rotterdam. Eur Urol. Nov. 2013;64(5):693-9.
Chun et al., Development and external validation of an extended 10-core biopsy nomogram. European Urology, 52:436-445 (2007).
Editorial (Toimitus-Ajankohtaista Lääkärin käsikirjasta): Eturauhassyöpä. Lääketieteellinen Aikakauskirja Duodecim, (1):99-102 (2012).
Eriksson et al., Dual-label time-resolved immunofluorometric assay of free and total prostate-specific antigen based on recombinant Fab fragments. Clin Chem. May 2000;46(5):658-66.
Genbank Accession No. 93091201. Feb. 2, 20113.
Gupta et al., A four-kallikrein panel for the prediction of repeat prostate biopsy: Data from the European Randomized Study of Prostate Cancer Screening in Rotterdam, Netherlands. Br. J. Cancer, 103:708-714 (2010).
Hara et al., Total and free prostate-specific antigen indexes in prostate cancer screening: value and limitation for Japanese populations. Asian J. Androl., 8(4):429-434 (2006).
Khan et al., Clinical utility of proPSA and "benign" PSA when percent free PSA is less than 15%. Urology, 64(6):1160-1164 (2004).
Lee et al., A meta-analysis of the performance characteristics of the free prostate-specific antigen test. Urology, 67(4):762-768 (2006).
Lilja et al., Prostate-specific antigen and prostate cancer: prediction, detection and monitoring. Nat. Rev. Cancer, 8(4):268-278 (2008).
Lilja et al., Prostate-specific antigen in serum occurs predominantly in complex with alpha 1-antichymotrypsin. Clin Chem. Sep. 1991;37(9):1618-25.

(56) References Cited

OTHER PUBLICATIONS

Lövgren et al., Enzymatic action of human glandular kallikrein 2 (hK2). Substrate specificity and regulation by Zn2+ and extracellular protease inhibitors. Eur J Biochem. Jun. 1999;262(3):781-9.

Lövgren et al., Production and activation of recombinant hK2 with propeptide mutations resulting in high expression levels. Eur J Biochem. Dec. 1999;266(3):1050-5.

Michielsen et al., Prediction of free PSA, PSA density and PSA density transition zone in the outcome of sextant prostate biopsies in patients with total PSA between 3 and 15 ng/ml. UroOncology, 4(2):71-76 (2004).

Nam et al., Assessing individual risk for prostate cancer. J. Clin. Oncol., 25(24):3582-3588 (2007).

Nam et al., Prospective multi-institutional study evaluating the performance of prostate cancer risk calculators. J. Clin. Oncol., 29(22):2959-2964 (2011).

Nam et al., Variants of the hK2 protein gene (KLK2) are associated with serum hK2 levels and predict the presence of prostate cancer at biopsy. Clin. Cancer Res., 12(21):6452-6458 (2006).

Nurmikko et al., Production and characterization of novel anti-prostate-specific antigen (PSA) monoclonal antibodies that do not detect internally cleaved Lys145-Lys146 inactive PSA. Clin Chem. Oct. 2000;46(10):1610-8.

Parekh et al., External validation of the Prostate Cancer Prevention Trial risk calculator in a screened population. Urology, 68(6):1152-1155 (2006).

Peltola et al., Immunoassay for the discrimination of free prostate-specific antigen (fPSA) forms with internal cleavages at $Lys_{(146)}$ or $Lys_{(146)}$ from fPSA without internal cleavages at $Lys_{(145)}$ or $Lys_{(146)}$. J Immunol Methods. Jun. 30, 2011;369(1-2):74-80. doi: 10.1016/j.jim.2011.04.006. Epub Apr. 28, 2011.

Peltola et al., Intact and internally cleaved free prostate-specific antigen in patients with prostate cancer with different pathologic stages and grades. Urology, 77(4):1009.e1-1009.e8 (2011).

Piironen et al., Determination and analysis of antigenic epitopes of prostate specific antigen (PSA) and human glandular kallikrein 2 (hK2) using synthetic peptides and computer modeling. Protein Sci. Feb. 1998;7(2):259-69.

Rajakoski et al., Epitope mapping of human prostate specific antigen and glandular kallikrein expressed in insect cells. Prostate Cancer Prostatic Dis. Sep. 1997;1(1):16-20.

Sokoll et al., A prospective, multicenter, National Cancer Institute Early Detection Research Network study of [-2]proPSA: improving prostate cancer detection and correlating with cancer aggressiveness. Cancer Epidemiol. Biomarkers Prev., 19(5):1193-1200 (2010).

Talvitie, Delfia immunoassays: Guide to Converting ELISA Assays to DELFIA. PerkinElmer Life and Analytical Sciences. Dec. 18, 2006:1-16. Retrieved on Jun. 11, 2015 from http://www.perkinelmer.com/cmsresources/images/man_delfia_elisa_conversion.pdf.

Thompson et al., Assessing prostate cancer risk: results from the prostate cancer prevention trial. J. Natl. Cancer Inst., 98:529-534 (2006).

Ulmert et al., Prostate-specific antigen at or before age 50 as a predictor of advance prostate cancer diagnosed up to 25 years later: A case-control study. BMC Medicine, 6(6):1-8 (2008).

Ulmert et al., Reproducibility and accuracy of measurements of free and total prostate-specific antigen in serum vs plasma after long-term storage at −20 degrees C. Clin. Chem., 52(2):235-239 (2006).

Van Vugt et al., Prediction of prostate cancer in unscreened men: external validation of a risk Calculator. Eur. J. Cancer 47(6):903-909 (2011).

Vickers et al., A four-kallikrein panel predicts prostate cancer in men with recent screening: Data from the European Randomized Study of Prostate Cancer Screening, Rotterdam. Clin. Cancer Res., 16(12):3232-3239 (2010).

Vickers et al., A panel of kallikrein marker predicts prostate cancer in a large, population-based cohort followed for 15 years without screening. Cancer Epidemiol. Biomarkers Prev., 20(2):255-261 (2011).

Vickers et al., A panel of kallikrein markers can reduce unnecessary biopsy for prostate cancer: Data from the European Randomized Study of Prostate Cancer Screening in Göteborg, Sweden. BMC Med., 6:19 (2008).

Vickers et al., Decision curve analysis: a novel method for evaluating prediction models. Med Decis Making. Nov.-Dec. 2006;26(6):565-74.

Vickers et al., Impact of recent screening on predicting the outcome of prostate cancer biopsy in men with elevated PSA: Data from the European Randomized Study of Prostate Cancer Screening in Gothenburg, Sweden. Cancer, 116(11):2612-2620 (2010).

Vickers et al., Reducing unnecessary biopsy during prostate cancer screening using a fourkallikrein panel: An independent replication. J. Clin. Oncol., 28(15):2493-2498 (2010).

Wenske et al., Evaluation of molecular forms of prostate-specific antigen and human kallikrein 2 in predicting biochemical failure after radical prostatectomy. Int J Cancer. Feb. 1, 2009;124(3):659-63. doi: 10.1002/ijc.23983.

[No Author Listed], Human Prostate-Specific Antigen (PSA) Kit Technical Data Sheet. AlphaLISA Research Reagents. Perkin Elmer. Waltham, MA. 2009. 9 pages.

[No Author Listed], Perkin Elmer Application Note. 2002. Last accessed May 15, 2017 from <http://www.perkinelmer.com/CMSResources/Images/46-72946BRO_Oncology.pdf>. 8 pages.

Chmielewski et al., Serum soluble CD36, assessed by a novel monoclonal antibody-based sandwich ELISA, predicts cardiovascular mortality in dialysis patients. Clin Chim Acta. Dec. 14, 2010;411(23-24):2079-82. doi: 10.1016/j.cca.2010.09.009. Epub Sep. 16, 2010.

Nurmikko et al., Discrimination of prostate cancer from benign disease by plasma measurement of intact, free prostate-specific antigen lacking an internal cleavage site at Lys145-Lys146. Clin Chem. Aug. 2001;47(8):1415-23.

Solovov et al., Estimation Effectiveness of Logistic Regression and Neural Network Analysis in Prostate Cancer Detection. Siberian Journal of Oncology. 2006;17(1):14-17.

Virtanen et al., Estimation of Prostate Cancer Probability by Logistic Regression: Free and Total Prostate-specific Antigen, Digital Rectal Examination, and Heredity Are Significant Variables. Clinical Chemistry. 1999;45(7):987-94.

Extended European Search Report for EP App. No. 15768735.1 mailed Jan. 23, 2018.

Extended European Search Report for EP App. No. 17187203.9 mailed Feb. 27, 2018.

Extended European Search Report for EP App. No. 17187202.1 mailed Feb. 16, 2018.

Azvolinsky, Study Confirms 4Kscore Accurately Predicts High-Grade Prostate Cancer. Cancer Network. Mar. 2, 2015. Last accessed on Jan. 29, 2018 from <http://www.cancernetwork.com/asco-genitourinary-cancers-symposium/study-confirms-4kscore-accurately-predicts-high-grade-prostate-cancer>. 2 pages.

Carter et al., Percentage of free prostate-specific antigen in sera predicts aggressiveness of prostate cancer a decade before diagnosis. Urology. May 1997;49(3):379-84.

Chuah et al., Ultrasensitive electrochemical detection of prostate-specific antigen (PSA) using gold-coated magnetic nanoparticles as 'dispersible electrodes'. Chem. Commun. 2012;48:3503-5. Epub Feb. 17, 2012.

Kaya et al., High-Sensitivity Immunoassay with Surface Plasmon Field-Enhanced Fluorescence Spectroscopy Using a Plastic Sensor Chip: Application to Quantitative Analysis of Total Prostate-Specific Antigen and GalNAcβ1-4GlcNAc-Linked Prostate-Specific Antigen for Prostate Cancer Diagnosis. Anal. Chem. 2015;87(3):1797-803. Epub Dec. 29, 2014.

Lilja et al., Long-Term Prediction of Prostate Cancer Up to 25 Years Before diagnosis of Prostate Cancer Using Prostate Kallikreins Measured at Age 44 to 50 Years. Journal of Clinical Oncology. Feb. 1, 2007;25(4):431-6.

Lin et al., PI-06 Late-Breaking Abstract: The 4Kscore Test as a Predictor of High Grade Prostate Cancer on Biopsy. The Journal of Urology. May 18, 2014;191(4S—Supplement):e224.

(56) References Cited

OTHER PUBLICATIONS

Mani et al., Ultrasensitive Immunosensor for Cancer Biomarker Proteins Using Gold Nanoparticle Film Electrodes and Multienzyme-Particle Amplification. ACS Nano. 2009;3(3):585-94. Epub Feb. 13, 2009.

Mathur et al., MP6-04 The 4KScore Test Predicts High-Grade Prostate Cancer on Biopsy with PSA Less Than 4 NG Per Millimeter. The Journal of Urology. May 15, 2015;191(4S—Supplement):e55.

Mitrunen et al., Dual-Label One-Step Immunoassay for Siumltaneous Measurement of Free and Total Prostate-Specific Antigen Concentrations and Ratios in Serum. Clin. Chem. 1995;41(8):1115-20.

O'Dowd et al., Analysis of Repeated Biopsy Results Within 1 Year After a Noncancer Diagnosis. Adult Urology. 2000;55(4):553-8.

Oesterling et al., Effect of cystoscopy, prostate biopsy, and transurethral resection of prostate on serum prostate-specific antigen concentration. Urology. Sep. 1993;42(3):276-82.

Parekh et al., A Multi-institutional Prospective Trial in the USA confirms that the 4Kscore Accurately Identifies Men with High-grade Prostate Cancer. European Urology. Sep. 2015;68:464-70.

Peng et al., Electrochemical immunoassay for the prostate specific antigen using ceria mesoporous nanospheres. Microchimica Acta. Oct. 2014;181(13-14):1505-12.

Pettersson et al., Free and complexed prostate-specific antigen (PSA): in vitro stability, epitope map, and development of immunofluorometric assays for specific and sensitive detection of free PSA and PSA-alpha 1-antichymotrypsin complex. Clin Chem. 1995;41(10):1480-8.

Punnen et al., PD38-03 The 4KScore is Associated with More Advanced Disease at Radical Prostatectomy; Results from a Multi-Institutional Prospective Trial. The Journal of Urology. May 18, 2015;193(4S, Supplement):e825.

Punnen, A multi-institutional prospective trial in the United States to confirm the 4Kscore identification of men with high-grade prostate cancer. 2015 Genitourinary Cancers Symposium. ASCO Meeting Library. Video Recording, Poster, and Abstract. Feb. 26, 2015. Video last accessed on Jan. 29, 2018 from <https://meetinglibrary.asco.org/record/106267/video>.

Seto et al., Development of ultra-high sensitivity bioluminescent enzyme immunoassay for prostate-specific antigen (PSA) using firefly luciferase. Luminescence. 2001;16:285-90. Epub Jul. 31, 2001.

Stephan et al., A (−5, −7) ProPSA Based Artificial Neural Network to Detect Prostate Cancer. European Urology. May 2006;50:1014-20.

Thaxton et al., Nanoparticle-based bio-barcode assay redefines "undetectable" PSA and biochemical recurrence after radical prostatectomy. PNAS. Nov. 2009;106(44):18437-42.

Väisänen et al., Development of Sensitive Immunoassays for Free and Total Human Glandular Kallikrein 2. Clinical Chemistry. Sep. 2004;50(9):1607-17.

Väisänen et al., Intact Free Prostate-Specific Antigen and Free and Total Human Glandular Kallikrein 2. Elimination of Assay Interference by Enzymatic Digestion of Antibodies to F(ab')2 Fragments. Anal. Chem. 2006;78(22):7809-15. Epub Oct. 17, 2006.

Vickers et al., A panel of kallikrein markers can reduce unnecessary biopsy for prostate cancer: Data from the European Randomized Study of Prostate Cancer Screening in Göteborg, Sweden. Journal of Urology. Apr. 1, 2008;179(4):719.

Vickers et al., The predictive value of prostate cancer biomarkers depends on age and time to diagnosis: Towards a biologically-based screening strategy. Int. J. Cancer. 2007;1221:2212-7. Epub Jul. 26, 2007.

[No Author Listed], 4Kscore Test. Opko Health, Inc. Dec. 5, 2014. 4 pages.

Kim et al., Potential Utility of Novel Biomarkers in Active Surveillance of Low-Risk Prostate Cancer. Biomed Research International. 2015;11 pages.

[No Author Listed], Delfia Research Reagents. Retrieved Dec. 1, 2019, from https://www.perkinelmer.com/lab-solution/resources/docs/BRO_DELFIAResearchReagents.pdf. 24 pages.

Armbruster et al., Limit of Blank, Limit of Detection, and Limit of Quantitation. Clin Biochem Rev. Aug. 2008;29:S49-52.

Bradley et al., Serum Antibodies to Huntington Interacting Protein-1: A New Blood Test for Porstate Cancer. Cancer Res. 2005;65(10):4126-33.

Etzioni et al., The case for early detection. Nat Rev Cancer. Apr. 2003;3(4):243-52.

Isharwal et al., ProPSA and diagnostic biopsy tissue DNA content combination improves accuracy to predict need for prostate cancer treatment among men enrolled in an active surveillance program. Urology. Mar. 2011;77(3):763.e1-6. doi: 10.1016/j.urology.2010.07.526. Epub Jan. 8, 2011.

Mercer, Use of multiple markers to enhance clinical utility. Immunol Ser. 1990;53:39-54.

Mitchell et al., Can High-Grade Prostate Cancer (Gleason 8-10) Be Cured With Definitive Local Therapy Without Testosterone Suppression? Five-Year Outcomes Employing Up-Front Prostatectomy in Patients With Clinically Localized, Nonmetastatic Disease. ARS 2015. Apr. 30, 2015;29(4). 2 pages.

Perez-Amodio et al., Effects of the ionic environment, charge, and particle surface chemistry for enhancing a latex homogeneous immunoassay of C-reactive protein. Anal Chem. Jul. 15, 2001;73(14):3417-25.

Soloway et al., Careful selection and close monitoring of low-risk prostate cancer patients on active surveillance minimizes the need for treatment. Eur Urol. Dec. 2010;58(6):831-5. doi: 10.1016/j.eururo.2010.08.027. Epub Aug. 20, 2010.

Steuber et al., Discrimination of benign from malignant prostatic disease by selective measurements of single chain, intact free prostate specific antigen. J Urol. Nov. 2002;168(5):1917-22. Erratum in: J Urol Jan. 2003;169(1):295.

Zhao et al., Interfacial recognition of human prostate-specific antigen by immobilized monoclonal antibody: effects of solution conditions and surface chemistry. J R Soc Interface. Oct. 7, 2012;9(75):2457-67. doi: 10.1098/rsif.2012.0148. Epub May 2, 2012.

Helbling et al., Indolent prostate cancer and active surveillance. Cancer World. Jan. 1, 2010;34:15-21.

Xiong, Clinical study of serum PSA and fPSA assayed by CLIA in diagnosing prostate disease. J Lab Med Clin Sci. 2005;2(5):198-9.

[No Author Listed], Early diagnosis and screening of prostate cancer. Perkin Elmer. DELFIA. Mar. 2003:4 pages.

Cui et al., Clinical significance of expression of PSA, hK2, PSMA in the peripheral blood of patients with prostate cancer. Chin J Oncol. Aug. 2004;26(8):479-81. Abstract Only.

Goluch et al., A microfluidic detection system based upon a surface immobilized biobarcode assay. Biosens Bioelectron. Apr. 15, 2009;24(8):2397-403. doi: 10.1016/j.bios.2008.12.017. Epub Dec. 24, 2008.

Li, Practicing Physicians' Regular Assessment and Guidance Book: Urology. China Med Sci Tech Press. Oct. 2014:6 pages.

Shariat et al., Beyond Prostate-Specific Antigen: New Serologic Biomarkers for Improved Diagnosis and Management of Prostate Cancer. Rev Urol. 2004;6(2):58-72.

Xu et al., Study of PSA, PSMA and hK2 mRNA in peripheral blood of prostate cancer patients and its clinical implications. J Peking Univ Health Sci. Apr. 2004;36(2):164-8.

Zhang et al., Research Progress of Tumor Markers for Prostatic Carcinoma. Modern Med Health. May 2011;27(19):2933-5.

Office Action for CN Application No. 201810035218.9 dated Apr. 1, 2022.

Ulmert et al., Rapid elimination kinetics of free PSA or human kallikrein-related peptidase 2 after initiation of gonadotropin-releasing hormone-antagonist treatment of prostate cancer: potential for rapid monitoring of treatment responses. Clin Chem Lab Med. Nov. 2012;50(11):1993-8. doi: 10.1515/cclm-2011-0967.

Zhang et al., Prostatic Cancer. Shijiazhuang: Hebei Science and Technology Publishing House. Jan. 31, 2007:392-4.

Park et al., Prostate vol. measurement by TRUS using heights obtained by transaxial and midsagittal scanning: comparison with

(56) References Cited

OTHER PUBLICATIONS specimen vol. following radical prostatectomy. Korean J Radiol. Apr.-Jun. 2000;1(2):110-3. doi: 10.3348/kjr.2000.1.2.110.
Punnen et al., Finding the Wolf in Sheep's Clothing: The 4Kscore Is a Novel Blood Test That Can Accurately Identify the Risk of Aggressive Prostate Cancer. Rev Urol. Jan. 1, 2015;17(1):3-13.
Extended European Search Report for EP App. No. 16787201.9 mailed Aug. 13, 2018.
Aly et al., Polygenic Risk Score Improves Prostate Cancer Risk Prediction: Results from the Stockholm-1 Cohort Study. European Urology. Jul. 2011;60(1):21-8. Epub Jan. 18, 2011.
Becker et al., Clinical Value of Human Glandular Kallikrein 2 and Free and Total Prostate-Specific Antigen in Serum from a Population of Men with Prostate-Specific Antigen Levels 3.0 ng/mL or Greater. Adult Urology. 2000;55:694-9.
Cybulski et al., A Novel Founder CHEK2 Mutation is Associated with Increased Prostate Cancer Risk. Cancer Research. Apr. 2004;64(8):2677-9.
Cybulski et al., NBS1 Is a Prostate Cancer Susceptibility Gene. Cancer Research. Feb. 2004;64(4):1215-9.
Ewing et al., Germline Mutations in HOXB13 and Prostate-Cancer Risk. The New England Journal of Medicine. Jan. 12, 2012;366:141-9.
Finlay et al., Development of Monoclonal Antibodies Specific for Human Glandular Kallikrein (hK2): Development of a Dual Antibody Immunoassay for hK2 with Negligible Prostate-Specific Antigen Cross-reactivity. Urology. May 1, 1998;51(5):804-9.
Fisher et al., Generation of monoclonal antibodies specific for human kallikrein 2 (hK2) using hK2-expressing tumors. The Prostate. May 2002;51(3):153-65. Epub Apr. 12, 2002.
Haese et al., Standardization of Two Immunoassays for Human Glandular Kallikrein 2. Clinical Chemistry. 2003;49(4):601-10.
Heidenreich et al., Guidelines on Prostate Cancer. Part 6: Diagnosis. European Association of Urology. Apr. 2010:14-27.
Henttu et al., cDNA coding for the entire human prostate specific antigen shows high homologies to the human tissue kallikrein genes. Biochemical and Biophysical Research Communications. Apr. 28, 1989;160(2):903-10.
Henttu et al., Prostate-specific Antigen and Human Glandular Kallikrein: Two Kallikreins of the Human Prostate. Annals of Medicine. 1994;26(3):157-64.
Kim et al., Detection of High Grade Prostate Cancer among PLCO Participants Using a Prespecified 4-Kallikrein Marker Panel. J Urol. Apr. 2017;197(4):1041-7.
Lee et al., A Highly Sensitive Porous Silicon (P-Si)-Based Human Kallikrein 2 (hK2) Immunoassay Platform toward Accurate Diagnosis of Prostate Cancer. Sensors. 2015;15:11972-87.
Leinonen et al., Epitope Mapping of Antibodies against Prostate-specific Antigen with Use of Peptide Libraries. Clinical Chemistry. Dec. 2002;48(12):2208-16.
Leinonen et al., Reactivity of anti-PSA monoclonal antibodies with recombinant human kallikrein-2. Tumour Biology. 1999;20(suppl 1):35-7.
Liton et al., Phage display aided improvement of a unique prostate-specific antigen (PSA) antibody unreactive with Lys145-Lys146 internally cleaved forms. J. Immunol. Methods. Jul. 2015;422:72-9.

Magi et al., Contribution of 32 GWAS-Identified Common Variants to Severe Obesity in European Adults Referred for Bariatric Surgery. PLoS One. Aug. 7, 2013;8(8):e70735. 9 pages.
Nahar et al., Among men with low-grade prostate cancer on prostate biopsy, the 4Kscore to predict prostate cancer aggressiveness at prostatectomy. Journal of Clinical Oncology. Jan. 2016;34(2):suppl 65.
Nilsson et al., Antigenic determinants of prostate-specific antigen (PSA) and development of assays specific for different forms of PSA. British Journal of Cancer. 1997;75:789-97.
Piironen et al., Immunofluorometric assay for sensitive and specific measurement of human prostatic glandular kallikrein (hK2) in serum. Clinical Chemistry. Jul. 1996;42(7):1034-41.
Punnen et al., A Multi-Institutional Prospective Trial Confirms Noninvasive Blood Test Maintains Predictive Value in African American Men. J Urol. Jun. 2018;199(6):1459-1463. doi: 10.1016/j.juro.2017.11.113. Epub Dec. 6, 2017.
Punnen et al., Among men with low-grade prostate cancer on prostate biopsy, the 4Kscore predicts the presence of more aggressive prostate cancer. EAU 2015. Madrid. Mar. 20-24, 2015. Abstract and Slides. 4 pages.
Punnen et al., The 4Kscore Predicts the Grade and Stage of Prostate Cancer in the Radical Prostatectomy Specimen: Results from a Multi-institutional Prospective Trial. European Urology Focus. Feb. 2015;3(1):94-9. Epub Jan. 6, 2016.
Selander et al., Serum Macrophage Inhibitory Cytokine-1 Concentrations Correlate with the Presence of Prostate Cancer Bone Metastases. Cancer Epidemiol Biomarkers Prev. 2007;16(3):532-7.
Shiiki et al., Association between saliva PSA and serum PSA in conditions with prostate adenocarcinoma. Biomarkers. 2011;16(6):498-503.
Stenman et al., Summary Report of the TD-3 Workshop: Characterization of 83 Antibodies against Prostate-Specific Antigen. Tumor Biology. 1999;20(suppl 1):1-12.
Steuber et al., Comparison of Free and Total Forms of Serum Human Kallikrein 2 and Prostate-Specific Antigen for Prediction of Locally Advanced and Recurrent Prostate Cancer. Clin Chem. Feb. 2007;53(2):233-40.
Tanase et al., Prostate cancer proteomics: Current trends and future perspectives for biomarker discovery. Oncotarget. 2017;8(11):18497-512.
Vickers et al., Prostate-Specific Antigen Velocity for Early Detection of Prostate Cancer: Result from a Large, Representative, Population-based Cohort. European Urology. Nov. 2009;56(5):753-60.
Vickers et al., The relationship between prostate-specific antigen and prostate cancer risk: the Prostate Biopsy Collaborative Group. Clin. Cancer Res. Sep. 2010;16(17):4374-81. Epub Aug. 24, 2010.
Wang et al., Western Blotting Analysis of Antibodies to Prostate-Specific Antigen: Specificities for Prostate-Specific Antigen and Prostate-Specific Antigen Fragments. Tumour Biology. 1999;20(suppl 1):79-85.
Wiklund et al., Macrophage inhibitory cytokine-1 (MIC-1/GDF15): a new marker of all-cause mortality. Aging Cell. 2010;9(6):1057-64.
Wilson et al., Fifth-Generation Digital Immunoassay for Prostate-Specific Antigen by Single Molecule Array Technology. Clinical Chemistry. 2011;57(12):1712-21.

* cited by examiner

COMPOSITIONS AND METHODS FOR ACTIVE SURVEILLANCE OF PROSTATE CANCER

RELATED APPLICATIONS

This application is a Continuation-in-Part of and claims priority to U.S. application Ser. No. 14/671,355, filed on Mar. 27, 2015, which claims priority to U.S. Provisional Application No. 61/972,099, filed Mar. 28, 2014, each of which is hereby incorporated by reference in its entirety for all purposes. This application also claims priority to U.S. Provisional Application No. 62/154,616, filed Apr. 29, 2015, which is hereby incorporated by reference in its entirety for all purposes.

BACKGROUND OF INVENTION

Elevated blood levels of total prostate-specific antigen (PSA) are associated with prostate-related disorders, including prostate cancer. There is considerable evidence that measuring levels of isoforms of PSA separately, rather than combining them together in a single measure of total PSA, leads to improved predictions relating to the presence of prostate cancer in a subject. There is also evidence that measurements of hK2, a molecule that converts PSA from its pro- to active form, are informative to such predictions. Moreover, multimarker panels based on such measurements have been proposed for assessing prostate cancer status in subject. However, there remains a need for improved methods for assessing prostate cancer, particularly for evaluating the need for invasive prostate tissue biopsies.

SUMMARY OF INVENTION

Aspects of the disclosure relate to improved methods for predicting whether a prostate tissue biopsy obtained from a subject will contain detectable prostate cancer of an aggressive form (e.g., Gleason score of greater than 6). Conventionally, subjects diagnosed as having non-aggressive prostate cancer are monitored for disease progression by obtaining prostate tissue biopsies periodically and evaluating them to determine whether or not the cancer has progressed to an aggressive form, in which case prostatectomy or radiotherapy or other treatment is indicated. Periodically obtaining prostate tissue biopsies is a clinically undesirable approach to monitoring because each biopsy involves an invasive procedure that is both costly and exposes the subject to potentially unnecessary surgical risks including infection, anesthesia complications, bleeding problems, blood clots, etc. Aspects of the disclosure, relate to a recognition that there is a need for a minimally invasive approach to monitoring subjects that have been diagnosed with non-aggressive disease. In particular, methods provided herein are useful for active surveillance of subjects that have been diagnosed as having a non-aggressive prostate cancer.

According to some aspects of the disclosure, methods are provided for evaluating a subject previously diagnosed as having non-aggressive prostate cancer (a low grade cancer, e.g., having a Gleason score of 6). In some embodiments, methods provided herein involve i) subjecting a blood sample of the subject to one or more immunoassays that measure levels of one or more kallikrein markers selected from: free prostate specific antigen (fPSA), intact prostate specific antigen (iPSA), total prostate specific antigen (tPSA) and human kallikrein 2 (hK2); and, in some embodiments, ii) determining the probability that a prostate tissue biopsy obtained from the subject would contain detectable aggressive prostate cancer (a high grade cancer, e.g., having a Gleason score of greater than 6) by weighting the measured one or more kallikrein marker levels and at least one clinical factor. In some embodiments, if the probability that the prostate tissue biopsy obtained from the subject would contain detectable aggressive prostate cancer is above a threshold level, a follow-up prostate tissue biopsy is obtained from the subject and analyzed to further evaluate presence of aggressive prostate cancer. In some embodiments, a non-aggressive prostate-cancer is associated with a Gleason score of 6. In some embodiments, an aggressive prostate cancer is associated with a Gleason score of 7 or more.

In some embodiments, the blood sample is obtained from the subject within 6 months to 12 months, 6 months to 24 months or 6 months to 36 months from an initial diagnosis of non-aggressive prostate cancer.

In some embodiments, methods provided herein involve repeating steps i) and ii) at least once, at least twice, at least three times, at least four times, at least five times, at least six times, at least seven times, at least eight times, at least nine times, or at least ten times. In some embodiments, methods provided herein involve repeating steps i) and ii) one to five times, two to five times, or two to ten times. In some embodiments, methods provided herein involve repeating steps i) and ii) at least once, at least twice, at least three times, at least four times, at least five times, at least six times, at least seven times, at least eight times, at least nine times, or at least ten times within 6 months to 12 months, 6 months to 24 months, or 6 months to 60 months from first performing steps i) and ii). In some embodiments, methods provided herein involve repeating steps i) and ii) at intervals of 6 months to 1 year. In some embodiments, methods provided herein involve repeating steps i) and ii) at least once per year for up to five years.

In some embodiments, the at least one clinical factor is the subject's age. In some embodiments, the at least one clinical factor is a parameter indicative of the outcome of a digital rectal examination performed on the subject. In some embodiments, the at least one clinical factor is selected from: number of prostate tissue biopsies performed on the subject to date; results of prior prostate tissue biopsies performed on the subject to date; occurrence of any negative biopsy since an initial diagnosis of non-aggressive prostate cancer; occurrence of any negative biopsy in one-year prior to obtaining the blood sample; total number of biopsies since an initial diagnosis of non-aggressive prostate cancer; prostate volume on prior biopsy; number of positive cores on prior biopsy; percent positive cores on prior biopsy; cross-sectional area of cancer in biopsy core sections; maximum cross-sectional area of cancer in any biopsy core sections; PSA density; race of subject; family history of prostate cancer; maximum percent of positive cores from any prior biopsy; and maximum number of positive cores from any prior biopsy.

In some embodiments, the probability that a subject has prostate cancer is further determined by weighting a cubic spline term based on the measured kallikrein marker level(s).

Further aspects of the disclosure relate to a method for determining a probability of an event associated with prostate cancer, the event being an upgrade from a non-aggressive prostate cancer to an aggressive prostate cancer. In some embodiments, the methods involve receiving, via an input interface, information indicative of levels of one or more kallikrein markers selected from: tPSA, fPSA, iPSA, and hK2 in a blood plasma sample of a subject previously diagnosed as having a non-aggressive prostate cancer; receiving, via an input interface, information about at least one clinical factor of the subject evaluating, using at least one processor, a logistic regression model based, at least in part, on the received information to determine a probability of an event associated with prostate cancer in the subject, wherein evaluating the logistic regression model comprises: determining the probability of the event associated with prostate cancer based, at least in part, on the information indicative of levels of one or more of tPSA, fPSA, iPSA, and hK2 and the information about the at least one clinical factor; and outputting an indication of the probability of the event associated with prostate cancer, Further aspects of the disclosure relate to a computer for determining a probability of an event associated with prostate cancer, the event being an upgrade from a non-aggressive prostate cancer to an aggressive prostate cancer. In some embodiments, the computer comprises an input interface configured to receive information indicative of levels of one or more kallikrein markers selected from: tPSA, fPSA, iPSA, and hK2 in a blood plasma sample of a subject and information about at least one clinical factor of the subject; at least one processor programmed to evaluate a logistic regression model based, at least in part, on the received information to determine a probability of an event associated with prostate cancer in the subject; and an output interface configured to output an indication of the probability of the event associated with prostate cancer, wherein the event associated with prostate cancer is an upgrade from a non-aggressive prostate cancer to an aggressive prostate cancer. In some embodiments, evaluating the logistic regression model comprises: determining the probability of the event associated with prostate cancer based, at least in part, on the information indicative of levels of one or more of tPSA, fPSA, iPSA, and hK2 and the information about the at least one clinical factor.

Further aspects of the disclosure relate to a system for determining a probability of an event associated with prostate cancer, the event associated with prostate cancer being an upgrade from a non-aggressive prostate cancer to an aggressive prostate cancer. In some embodiments, the system comprises: a) a detector configured to measure levels of one or more kallikrein markers selected from: tPSA, fPSA, iPSA, and hK2 in a blood plasma sample of a subject; and b) a computer in communication (e.g., electronic communication or wireless communication) with the detector. In some embodiments, the computer includes an input interface configured to receive information from the detector indicative of the measured levels of one or more of tPSA, fPSA, iPSA, and hK2, and to receive information about at least one clinical factor of the subject; at least one processor programmed to evaluate a logistic regression model based, at least in part, on the received information to determine a probability of an event associated with prostate cancer in the subject; and an output interface configured to output an indication of the probability of the event associated with prostate cancer. In some embodiments, evaluating the logistic regression model involves: determining the probability of the event associated with prostate cancer based, at least in part, on the information indicative of levels of one or more of tPSA, fPSA, iPSA, and hK2 and the information about the at least one clinical factor.

Still further aspects of the disclosure relate to a computer-readable storage medium encoded with a plurality of instructions that, when executed by a computer, perform a method for determining a probability of an event associated with prostate cancer, the event being an upgrade from a non-aggressive prostate cancer to an aggressive prostate cancer. In some embodiments, the method involves evaluating a logistic regression model based, at least in part, on information indicative of levels of one or more kallikrein marker selected from: tPSA, fPSA, iPSA, and hK2 in a blood plasma sample of a subject and information about at least one clinical factor of the subject to determine a probability of an event associated with prostate cancer in the subject, and outputting an indication of the probability of the event associated with prostate cancer. In some embodiments, evaluating the logistic regression model involves: determining the probability of the event associated with prostate cancer based, at least in part, on the information indicative of levels of one or more of tPSA, fPSA, iPSA, and hK2 and the information about the at least one clinical factor.

DETAILED DESCRIPTION OF INVENTION

Figure 1A:
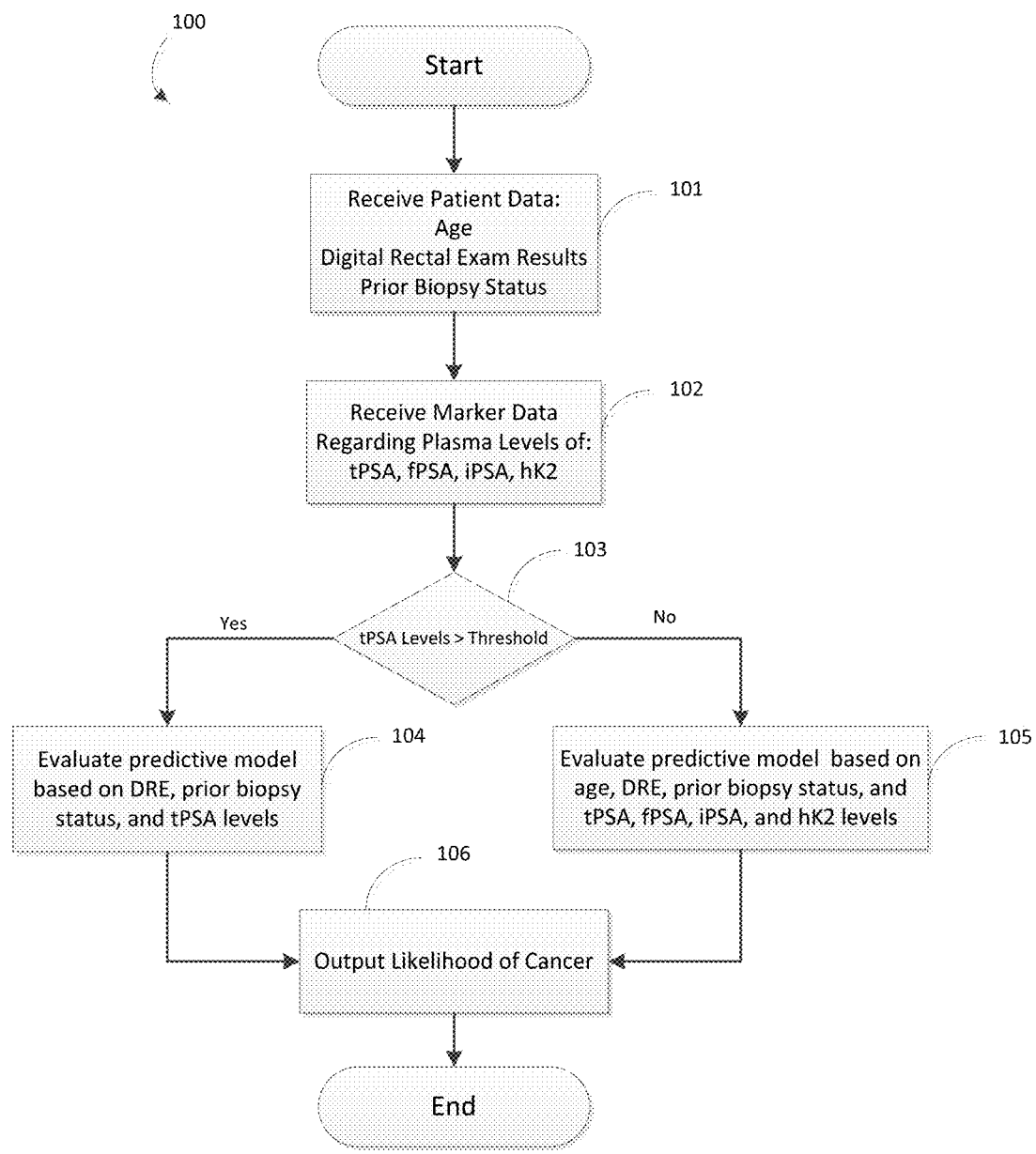
FIG. 1A is a non-limiting schematic showing a process for determining the probability that a biopsy will contain detectable prostate cancer (e.g., a detectable aggressive prostate cancer)

Aspects of the disclosure relate to improved methods for predicting whether a prostate tissue biopsy obtained from a subject previously diagnosed with non-aggressive prostate cancer will contain detectable prostate cancer, including high grade prostate cancer (Gleason 7 or greater). Thus, methods disclosed herein may be employed by a healthcare provider for purposes of determining whether a prostate tissue biopsy is merited for a subject being monitored to detect progression to an aggressive prostate cancer. In some embodiments, the methods involve using a blood sample obtained from a subject to conduct one or more immunoassays that measure levels of prostate specific antigens, such as one or more of the following kallikrein markers: total prostate-specific antigen (tPSA), free prostate specific antigen (fPSA), intact prostate specific antigen (iPSA) and/or human Kallikrein 2 (hK2). In some embodiments, a predictive model (e.g., a logistic regression model) is provided that incorporates plasma levels of tPSA, fPSA, iPSA and/or hK2 to determine the probability that a prostate tissue biopsy will contain detectable cancer, particularly aggressive prostate cancer. Moreover, in some embodiments, it has been found that improved predictive results can be obtained by combining information regarding measured prostate specific antigen levels with one or more clinical factors, particularly information concerning whether or not a subject has had a prior biopsy to detect the presence of prostate cancer. Accordingly, improved methods are provided that are useful for determining whether a subject should undergo an invasive prostate tissue biopsy.

Aspects of the disclosure provide methods of determining the probability that a prostate tissue biopsy obtained from a subject would contain detectable prostate cancer, e.g., aggressive prostate cancer. Such methods may involve subjecting a blood plasma sample of a subject to an immunoassay that measures at least a level of total prostate specific antigen (tPSA) in the blood plasma sample. If the tPSA level is above a threshold level, then the probability that a prostate tissue biopsy would contain detectable prostate cancer may be determined by weighting the measured level of tPSA and a parameter indicative of whether the subject has had a prior biopsy of prostate tissue. On the other hand, if the tPSA level is at or below the threshold level, then the probability that a prostate tissue biopsy would contain detectable prostate cancer may be determined by weighting measured levels of tPSA, fPSA, iPSA, and hK2 and a parameter indicative of whether the subject has had a prior biopsy of prostate tissue. Accordingly, in some embodiments, methods provided herein may involve subjecting the blood plasma sample to an immunoassay that measures levels of free prostate specific antigen (fPSA), intact prostate specific antigen (iPSA), and/or human kallikrein 2 (hK2) in the blood plasma sample. In some embodiments, the probability is further determined by weighting a parameter indicative of the subject's age. In some embodiments, the probability is further determined by weighting at least one clinical factors, such as, for example, one or more parameters indicative of the outcome of a digital rectal examination performed on the subject. In some embodiments, the at least one clinical factor is selected from: number of prostate tissue biopsies performed on the subject to date; results of prior prostate tissue biopsies performed on the subject to date; occurrence of any negative biopsy since an initial diagnosis of non-aggressive prostate cancer; occurrence of any negative biopsy in one-year prior to obtaining the blood sample; total number of biopsies since an initial diagnosis of non-aggressive prostate cancer; prostate volume on prior biopsy; number of positive cores on prior biopsy; percent positive cores on prior biopsy; cross-sectional area of cancer in biopsy core sections; maximum cross-sectional area of cancer in any biopsy core sections; PSA density; race of subject; family history of prostate cancer; maximum percent of positive cores from any prior biopsy; and maximum number of positive cores from any prior biopsy.

In some embodiments, the threshold level of tPSA used for model selection is a level that indicates whether using tPSA alone, or together with certain patient specific information (e.g., prior biopsy status), would be sufficient for purposes of establishing a probability that a prostate tissue biopsy would contain detectable prostate cancer. In some embodiments, the threshold level is 5 ng/mL, 10 ng/mL, 15 ng/mL, 20 ng/mL, 25 ng/mL, 30 ng/mL, 35 ng/mL or 40 ng/mL. Because tPSA levels combined with certain patient specification information, particularly prior biopsy status, may be enough to make informative predictions, in some embodiments, it may be cost effective not to perform immunoassays to detect other antigens before first determining levels of tPSA. However, in some embodiments, levels of tPSA may be determined in parallel or together with other marker levels, e.g., fPSA, iPSA, or hK2.

In some embodiments, multiple kallikrein marker levels (e.g., levels of two or more of tPSA, fPSA, iPSA, and hK2) are determined in parallel in the same assay. In other embodiments, such antigen levels are determined in separate assays. In some embodiments, antigen levels are determined from the same original blood draw (e.g., a venous blood draw) from a subject. In some embodiments, antigen levels are determined from different blood draws. In some embodiments, antigen levels are determined using plasma preparations from the same or different blood draws. In some embodiments, one or more antigen levels are determined using a plasma preparation and one or more other antigens are determined using a different type of blood preparation, e.g., serum. Blood plasma is a pale-yellow liquid component of blood. In some embodiments, blood plasma may be prepared by spinning a tube of blood containing an anticoagulant (e.g., Heparin, EDTA, etc.) in a centrifuge until blood cells and debris move to the bottom of the tube, after which the blood plasma may be poured or drawn off.

Methods are provided herein for determining whether a subject is a candidate for a prostate tissue biopsy. Such methods may involve a physician or health care provider obtaining a blood sample from a subject and determining the probability that the prostate tissue biopsy would contain detectable prostate cancer (e.g., aggressive prostate cancer) based, at least in part, on measured levels of antigens determined using the blood sample. The blood sample may be processed locally (e.g., within the same health care facility or business that the subject is being evaluated) or may send it out to an external or third-party laboratory or facility for processing and analysis. If a tPSA level measured using the blood sample is above a threshold level, the probability is determined based on weighting the tPSA level. Otherwise, if the tPSA level is at or below the threshold level, the probability is based on weighting levels of tPSA, fPSA, iPSA, and hK2 measured using the blood sample. In either case, the probability is typically also based on weighting at least one clinical factors, such as, for example, a parameter indicative of whether the subject had a prior biopsy of prostate tissue. The physician or healthcare provider may determine whether the subject is a candidate for the prostate tissue biopsy based on the probability that the prostate tissue biopsy will contain detectable prostate cancer.

In some embodiments, a physician or healthcare provider may set a probability cut-off (threshold level) in which a biopsy will be indicated if a probability is at or above the cut-off. For example, if the probably is greater than 5%, 6%, 6.5%, 7%, 7.5%, 8%, 8.5%, 9%, 9.5%, 10%, 12.5%, 15%, 20%, 25%, 0.30%, 35%, 40%, 45%, 50%, 55%, 60%, 65%, 70%, 75%, 80%, 85%, 90%, 95%, 99%, or more, then the physician or healthcare provider may determine that the subject is a candidate for the prostate tissue biopsy. In some embodiments, a cut-off (threshold level) based on a probability that a prostate tissue biopsy will contain detectable aggressive prostate cancer (e.g., a Gleason score of 7 or greater) is 5%, 6%, 6.5%, 7%, 7.5%, 8%, 8.5%, 9%, 9.5%, 10%, 12.5%, or 15%. In some embodiments, a cut-off (threshold level) based on a probability that a prostate tissue biopsy will contain detectable prostate cancer of any grade is 10%, 12.5%, 15%, 20%, 25%, or 30%. In some embodiments, if a probability is below a cut-off then a physician or healthcare provider will not order a biopsy but will continue to monitor the subject, e.g., for increases in probability levels or changes in other risk factors indicative of prostate cancer.

In some embodiments, if a subject is determined to be a candidate for a prostate tissue biopsy, then the physician or health care provider may obtain or order to be obtained a prostate tissue biopsy from the subject and determine whether the subject has prostate cancer based on an analysis of the prostate tissue biopsy. The prostate tissue biopsy may be analyzed using any appropriate method including, for example, a cytological or histological analysis. The tissue sample may be characterized based on its clinical stage of cancer. The sample may be characterized based on a Gleason grade. Gleason 3+3 (6.0) corresponds to a tumor of low grade and a favorable prognosis. Gleason 3+4 (7.0) and 3+5 (8.0) typically correspond to tumors that have tissue of primarily low grade transformation with some high grade transformation. Gleason 4+3 (7.0) and 5+3 (8.0) typically correspond to tumor that have tissue of primarily high grade transformation with some low grade transformation. Gleason 4+4 (8.0), 4+5 (9.0), (9.0), and 5+5 (10.0) corresponds to high grade tumors. Accordingly, in some embodiments, the prostate cancer comprises high grade cancer (e.g., Gleason ≥7.0).

Immunoassays

Levels of prostate specific antigens (e.g., kallikrein markers: tPSA, iPSA, fPSA, and/or hK2) can be assessed by any appropriate method. In some embodiments, antibodies or antigen-binding fragments are provided that are suited for use in immunoassays. Immunoassays utilizing such antibody or antigen-binding fragments may competitive and non-competitive immunoassays in either a direct or indirect formats. Non-limiting examples of such immunoassays are Enzyme Linked Immunoassay (ELISA), radioimmunoassay (RIA), sandwich assay (immunometric assay), flow cytometry, western blot assay, immunoprecipitation assays, immunohistochemistry, immuno-microscopy, lateral flow immuno-chromatographic assays, and proteomics arrays. Antigens or antibodies or antigen-binding fragments that bind to them can be immobilized, e.g., by binding to solid supports (e.g., carriers, membrane, columns, proteomics array, etc.). Examples of solid support materials include glass, polystyrene, polyvinyl chloride, polyvinylidene difluoride, polypropylene, polyethylene, polycarbonate, dextran, nylon, amyloses, natural and modified celluloses, such as nitrocellulose, polyacrylamides, agaroses, and magnetite. The nature of the support can be either fixed or suspended in a solution (e.g., beads).

In some embodiments, labeled antibodies or antigen binding fragments may be used as tracers to detect antigen bound antibody complexes. Examples of the types of labels which can be used to generate tracers include enzymes, radioisotopes, colloidal metals, fluorescent compounds, magnetic, chemiluminescent compounds, and bioluminescent compounds. Radiolabeled antibodies are prepared in known ways by coupling a radioactive isotope such as $^{153}$Eu, $^{3}$H, $^{32}$P, $^{35}$S, $^{59}$Fe, or $^{125}$I, which can then be detected by gamma counter, scintillation counter or by autoradiography. As discussed herein, antibodies and antigen-binding fragments may alternatively be labeled with enzymes such as yeast alcohol dehydrogenase, horseradish peroxidase, alkaline phosphatase, and the like, then developed and detected spectrophotometrically or visually. Suitable fluorescent labels include fluorescein isothiocyanate, fluorescamine, rhodamine, and the like. Suitable chemiluminescent labels include luminol, imidazole, oxalate ester, luciferin, and others.

An immunoassay may comprise contacting the sample, e.g., a plasma sample, containing an antigen with an antibody, or antigen-binding fragment (e.g., F(ab), F(ab)$_2$), under conditions enabling the formation of binding complexes between antibody or antigen-binding fragment and antigen. In some embodiments, a plasma sample is contacted with an antibody or antigen-binding fragment under conditions suitable for binding of the antibody or antigen-binding fragment to a target antigen, if the antigen is present in the sample. This may be performed in a suitable reaction chamber, such as a tube, plate well, membrane bath, cell culture dish, microscope slide, and other chamber. In some embodiments, an antibody or antigen-binding fragment is immobilized on a solid support. An antibody or antigen binding fragments that binds to an antigen in a sample may be referred to as a capture antibody. In some embodiments, the capture antibody comprises a tag (e.g., a biotin label) that facilitates its immobilization to a solid support by an interaction involving the tag (e.g., a biotin-streptavidin interaction in which the streptavidin is immobilized to a solid support). In some embodiments, the solid support is the surface of a reaction chamber. In some embodiments, the solid support is of a polymeric membrane (e.g., nitrocellulose strip, Polyvinylidene Difluoride (PVDF) membrane, etc.). In other embodiments, the solid support is a biological structure (e.g., bacterial cell surface). Other exemplary solid supports are disclosed herein and will be apparent to one of ordinary skill in the art.

In some embodiments, the antibody and antigen-binding fragment is immobilized on the solid support prior to contacting with the antigen. In other embodiments, immobilization of the antibody and antigen-binding fragment is performed after formation of binding complexes. In still other embodiments, antigen is immobilized on a solid support prior to formation of binding complexes. In some embodiments, a tracer may be added to the reaction chamber to detect immobilized binding complexes. In some embodiments, the tracer comprises a detectably labeled secondary antibody directed against the antigen. In some embodiments, the tracer comprises a detectably labeled secondary antibody directed against the capture antibody. In some embodiments, the primary antibody or antigen-binding fragment is itself detectable labeled.

In one embodiment, immunoassay methods disclosed herein comprise immobilizing antibodies or antigen-binding fragments to a solid support; applying a sample (e.g., a plasma sample) to the solid support under conditions that permit binding of antigen to the antibodies or antigen-binding fragment, if present in the sample; removing the excess sample from the solid support; applying a tracer (e.g., detectably labeled antibodies or antigen-binding fragments) under conditions that permit binding of the tracer to the antigen-bound immobilized antibodies or antigen-binding fragments; washing the solid support and assaying for the presence tracer.

In some embodiments, the antibody and antigen-binding fragment is immobilized on the solid support after contacting with the antigen in a reaction chamber. In some embodiments, the antibody and antigen-binding fragment is immobilized on the solid support prior to contacting with the antigen in a reaction chamber. In either case, a tracer may be added to the reaction chamber to detect immobilized binding complexes. In some embodiments, a tracer comprises a detectably labeled secondary antibody directed against the antigen. In some embodiments, the tracer comprises a detectably labeled secondary antibody directed against the primary antibody or antigen-binding fragment. As disclosed herein, the detectable label may be, for example, a radio-isotope, a fluorophore, a luminescent molecule, an enzyme, a biotin-moiety, an epitope tag, or a dye molecule. Suitable detectable labels are described herein.

In some embodiments, it has been found that performing certain immunoassays in low pH buffer leads to more sensitive antigen detection. Accordingly, in some embodiments, a tracer antibody is contacted with a capture antibody in a buffer having a pH in a range of 6.5 to less than 7.75 such that the tracer binds to the capture-antibody-antigen complex. In some embodiments, the buffer pH is about 6.5, 6.6, 6.7, 6.8, 6.9, 7.0, 7.1, 7.2, 7.3, 7.4, 7.5, or 7.6.

It should be appreciated that in any of the assays disclosed herein capture antibodies may be swapped with tracer antibodies.

In some embodiments, an immunoassay that measures the level of fPSA involves contacting fPSA present in the plasma blood sample with a capture antibody specific for fPSA under conditions in which the first capture antibody binds to fPSA, thereby producing a capture-antibody-fPSA complex; and detecting the capture-antibody-fPSA complex using a tracer. The capture antibody may be a H117 antibody. In some embodiments, the tracer comprises a 5A10 antibody or fragment thereof (e.g., a F(ab) fragment).

In some embodiments, an immunoassay that measures the level of iPSA involves contacting iPSA present in the plasma blood sample with a capture antibody specific for free PSA, which includes iPSA and nicked PSA, under conditions in which the second capture antibody binds at least to iPSA, thereby producing a capture-antibody-iPSA complex and detecting the capture-antibody-iPSA complex using a second tracer. In some embodiments, the tracer comprises a 4D4 antibody. In some embodiments, the capture antibody is a 5A10 antibody or fragment thereof (e.g., a F(ab) fragment).

In some embodiments, an immunoassay that measures the level of tPSA involves contacting tPSA present in the plasma blood sample with a capture antibody specific for tPSA under conditions in which the third capture antibody binds to tPSA, thereby producing a capture-antibody-tPSA complex; and detecting the capture-antibody-tPSA complex using a third tracer. In some embodiments, the tracer comprises a H50 antibody. In some embodiments, the capture antibody is a H117 antibody.

In some embodiments, an immunoassay that measures the level of hK2 involves contacting PSA in the plasma blood sample with blocking antibodies specific for PSA; contacting hK2 present in the plasma blood sample with a fourth capture antibody specific for hK2 under conditions in which the fourth capture antibody binds to hK2, thereby producing a capture-antibody-hK2 complex; and detecting the capture-antibody-hK2 complex using a fourth tracer. In some embodiments, the tracer comprises a 7G1 antibody. In some embodiments, the capture antibody is a 6H10 F(ab)$_2$. In some embodiments, the blocking antibodies comprise a 5H7 antibody, a 5H6 antibody, and a 2E9 antibody.

Table 0 below lists antibodies and antigen-binding fragments that may be used in the methods disclosed herein and their corresponding epitopes.

TABLE 0

Antibodies and Epitopes/Sources of Antibodies

| Antibody Name | Epitope | Reference or Source |
|---|---|---|
| F(ab)$_2$ 6H10 | | Becker et al. 2000. Sensitive and Specific Immunodetection of Human Glandular Kallikrein 2 in Serum. Clin Chem. 46(2), 198-206. |
| 2E9 | amino acids 79-93 and/or 80-91 of PSA protein | Lilja et al. 1991. Prostate-Specific Antigen in Serum Occurs Predominantly in Complex with alpha-1-Antichymotrypsin. Clin Chem. 37(9), 1618-1625. Piironen, et al. Determination and analysis of antigenic epitopes of prostate specific antigen (PSA) and human glandular kallikrein 2 (hK2) using synthetic peptides and computer modeling. Protein Science (1998), 7: 259-269 |

TABLE 0-continued

Antibodies and Epitopes/Sources of Antibodies

| Antibody Name | Epitope | Reference or Source |
|---|---|---|
| 5F7 | | Nurmikko et al. 2000. Production and Characterization of Novel Anti-Prostate-specific Antigen (PSA) Monoclonal Antibodies That Do Not Detect Internally Cleaved Lys145-Lys146 Inactive PSA. Clin Chem. 46(10): 1610-1618. |
| 5H6 | amino acids 225-237 of PSA protein | Nurmikko et al. 2000. Supra |
| 7G1 | | Nurmikko et al. 2000. Supra |
| Fab 5A10 | amino acids 75-89, 80-94 and/or 82-39 of PSA protein | Eriksson et al. 2000. Dual-label time-resolved immunofluorometric assay of free and total Prostate-specific Antigen Based on Recombinant Fab Fragments. Clin Chem 46(5), 658-666. Piironen et al. Supra |
| 4D4 | amino acids 130-144 of PSA protein | U.S. Pat. No. 7,872,104 |
| H117 | | U.S. Pat. No. 5,672,480 |
| H50 | | U.S. Pat. No. 5,672,480 |
| 5A10 | amino acids 75-89, 80-94 and/or 82-39 of PSA protein | U.S. Pat. No. 5,939,533, European Collection of Animal Cell Cultures Accession number 93091201. Piironen et al. Supra |

Microfluidic Sample Analyzers

It should be appreciated that any of the immunoassay methods disclosed herein may be performed or implemented using a microfluidic device (e.g., a cassette) and/or a microfluidic sample analyzer. For example, a microfluidic device may be used to determine one or more characteristics of kallikrein markers (e.g., levels of tPSA, fPSA, iPSA, or hK2). In some embodiments, a system may include a microfluidic sample analyzer, which for example, may be configured to analyze a sample provided in a cassette having one or more microfluidic channels for containing and/or directing flow of a sample that comprises immunoassay components (e.g., antigen-antibody complexes, tracers, etc.). In some embodiments, an analyzer comprises an optical system including one or more light sources and/or one or more detectors configured for measuring levels of antigen-antibody complexes and/or tracers present in one or more microfluidic channels. Furthermore, in some embodiments, systems are provided, which may include a processor or computer programmed to evaluate a predictive model (e.g., a logistic regression model) in electronic communication with a microfluidic device and/or a microfluidic sample analyzer or other device for determining a probability of an event associated with prostate cancer based on levels of markers (e.g., levels of tPSA, fPSA, iPSA, or hK2).

In one particular example, a system includes a microfluidic sample analyzer comprising a housing and an opening in the housing configured to receive a cassette having at least one microfluidic channel, wherein the housing includes a component configured to interface with a mating component on the cassette to detect the cassette within the housing. The system also includes a pressure-control system positioned within the housing, the pressure-control system configured to pressurize the at least one microfluidic channel in the cassette to move the sample through the at least one microfluidic channel. The system further includes an optical system positioned within the housing, the optical system including at least one light source and at least one detector spaced apart from the light source, wherein the light source is configured to pass light through the cassette when the cassette is inserted into the sample analyzer and wherein the detector is positioned opposite the light source to detect the amount of light that passes through the cassette. The system may include a user interface associated with the housing for inputting at least one clinical factor (e.g., the age of a person). The system may include a processor in electronic communication with the microfluidic sample analyzer, the processor programmed to evaluate a logistic regression model as described herein in combination with information indicative of levels of one or more kallikrein markers selected from: tPSA, fPSA, iPSA, and hK2 in a blood plasma sample of a subject previously diagnosed as having a non-aggressive prostate cancer.

Non-limiting examples of suitable microfluidic devices are disclosed in US Patent Application Publication Number US 2013/0273643, entitled "METHODS AND APPARATUSES FOR PREDICTING RISK OF PROSTATE CANCER AND PROSTATE GLAND VOLUME," which published on Oct. 17, 2013, and U.S. Pat. No. 8,765,062, entitled "Systems and Devices for Analysis of Samples", which issued on Jul. 1, 2014, the contents of which are incorporated herein by reference in their entirety for all purposes. It should be appreciated, however, that other types of device may also be used (e.g., plate readers, analyzers for microwell ELISA-type assays, etc.) as the disclosure is not limited in this respect.

Predictive Models and Computer Implemented Methods

Aspects of the disclosure provide computer implemented methods for determining a probability of an event associated with prostate cancer, such as an upgrade from non-aggressive to aggressive prostate cancer. Such methods may involve receiving, via an input interface, information indicative of the level of tPSA present in a blood plasma sample of a subject and receiving, via an input interface, information about whether the subject had a prior biopsy of prostate tissue. In some embodiments, the methods further involve evaluating, using at least one processor, a suitable predictive model (e.g., a logistic regression model) based, at least in part, on the received information to determine a probability of the event associated with prostate cancer in the subject. The predictive model may generate the probability of the event associated with prostate cancer based, at least in part, on measured levels of tPSA and information about whether the subject had a prior biopsy of prostate tissue. The predictive model may generate the probability of the event associated with prostate cancer based, at least in part, on measured levels of tPSA, fPSA, iPSA, and hK2 and information about whether the subject had a prior biopsy of prostate tissue.

FIG. 1 illustrates a flowchart of a process 100 in accordance with some embodiments of the disclosure. In step 101, one or more values representing patient data corresponding to age, digital examination status and/or prior biopsy status are received by at least one processor for processing using one or more of the techniques described herein. In step 102 one or more values representing marker data for tPSA, fPSA, iPSA, and/or hK2 are received by the at least one processor. The values may be received in any suitable way including, but not limited to, through a local input interface such as a keyboard, touch screen, microphone, or other input device, from a network-connected interface that receives the value(s) from a device located remote from the processor(s), or directly from one or more detectors that measure the blood marker value(s) (e.g., in an implementation where the processor(s) are integrated with a measurement device that includes the one or more detectors).

In step 103, after receiving the value(s) for tPSA, the process proceeds such that if levels of tPSA are above a threshold (e.g., 25 ng/mL), then a first predictive model is selected and, if levels of tPSA are at or below the threshold, then a second predictive model is selected. Accordingly, at step 104, if the levels of tPSA are above the threshold level then a predictive model is selected that is based DRE status, prior biopsy status and tPSA levels. Alternatively, at step 105, if the levels of tPSA are at or below the threshold level, then a predictive model is selected based on DRE status, prior biopsy status and tPSA, fPSA, iPSA and hK2 levels. The predictive model of step 104, 105 is used to determine the probability that a subject has a prostate cancer. The prediction may be for a cancer of any grade or for a cancer of high grade or for an upgrade from non-aggressive to aggressive prostate cancer depending on the model used.

After determining a probability of an event associated with prostate cancer (e.g., an upgrade from non-aggressive prostate cancer to aggressive prostate cancer), the process proceeds to step 106, where the probability is output to a user (e.g., a physician, a patient) to guide a further diagnostic procedure and/or treatment decisions. The probability may be output in any suitable way. For example, in some embodiments, the probability may be output by displaying a numeric value representing the probability on a display screen of a device. In other embodiments, the probability may be output using one or more lights or other visual indicators on a device. In yet other embodiments, the probability may be provided using audio output, tactile output, or some combination of one or more of audio, tactile, and visual output. In some embodiments, outputting the probability comprises sending information to a network-connected device to inform a user about the determined probability. For example, the probability may be determined by one or more processors located at a remote site, and an indication of the probability may be sent to an electronic device of a user (e.g., a physician) using one or more networks, in response to determining the probability at the remote site. The electronic device that provides output to a user in accordance with the techniques described herein may be any suitable device including, but not limited to, a laptop, desktop, or tablet computer, a smartphone, a pager, a personal digital assistant, and an electronic display.

In some embodiments, the probability of the event associated with prostate cancer is determined in accordance with equation (I), reproduced below:

$$\text{Probability} = \frac{e^L}{1+e^L} \tag{1}$$

where the logit (L) is determined using any of a plurality of logistic regression models. Non-limiting examples of different types of logistic regression models that may be used in accordance with the techniques described herein include:

1. Simple Model (tPSA Only)

$$L = \beta_0 + \beta_1(\text{Age}) + \beta_2(\text{tPSA}) + \beta_3(\text{priorbx}) \tag{2}$$

or $$L = \beta_0 + \beta_1 \text{tpsa} + \beta_2 \text{dre}_{neg} + \beta_3 \text{dre}_{pos} + \beta_4 \text{priorbx} \tag{3}$$

2. Four Assay Model Using Free/Total Ratio

In this model, the ratio of free PSA to total PSA is substituted for the free PSA term.

$$L = \beta_0 + \beta_1(\text{Age}) + \beta_2(tPSA) + \tag{4}$$

$$\beta_3\left(\frac{fSPA}{tPSA}\right) + \beta_4(iPSA) + \beta_5(hK2) + \beta_6(priorbx)$$

3. Four Assay Model Using Log(tPSA) and Free/Total Ratio

In this model, the log of tPSA is substituted for the tPSA term to account for the increased contribution of this predictive factor.

$$L = \beta_0 + \beta_1(\text{Age}) + \beta_2(\log[tPSA]) + \tag{5}$$

$$\beta_3\left(\frac{fPSA}{tPSA}\right) + \beta_4(iPSA) + \beta_5(hK2) + \beta_6(priorbx)$$

4. Polynomial Model

In this model, additional non-linear terms for tPSA and fPSA are included. In the example equation provided below, the square of tPSA is used to emphasize the direct relationship between this term and risk of prostate cancer, and the square root of the free/total PSA term is used to reflect the inverse association of this term with risk. It should be appreciated however, that polynomial terms of higher order (e.g., cubic) may also be included in some embodiments.

$$L = \beta_0 + \beta_1(\text{Age}) + \beta_2(tPSA) + \beta_3(fPSA) + \tag{6}$$

$$\beta_4(iPSA) + \beta_5(hK2) + \beta_6(tPSA^2) + \beta_7\left(\sqrt{\frac{fPSA}{tPSA}}\right) + \beta_8(priorbx)$$

5. Linear Splines for all Four Assays

In this model, linear splines are added, with a single knot at the median value. The splines may be determined using the following equations:

$sp1(x)=x$ if $x<\text{knot}$ $sp1(x)=\text{knot}$ if $x\geq\text{knot}$ $sp2(x)=0$ if $x<\text{knot}$ $sp2(x)=x-\text{knot}$ if $x\geq\text{knot}$ \hfill (7)

with the model being represented as:

$$L = \beta_0 + \beta_1(\text{Age}) + \beta_2(tPSA) + \beta_3(fPSA) + \tag{8}$$

$$\beta_4(iPSA) + \beta_5(hK2) + \beta_6(sp1[tPSA]) + \beta_7(sp2[tPSA]) +$$

$$\beta_8(sp1[fPSA]) + \beta_9(sp2[fPSA]) + \beta_{10}(sp1[iPSA]) +$$

$$\beta_{11}(sp2[iPSA]) + \beta_{12}(sp1[hK2]) + \beta_{13}(sp2[hK2]) + \beta_{14}(priorbx)$$

6. Linear Splines for tPSA and fPSA

In this model, linear splines are included only for tPSA and fPSA to reduce the number of variables and simplify the model.

$$L=\beta_0+\beta_1(\text{Age})+\beta_2(tPSA)+\beta_3(fPSA)+\beta_4(iPSA)+\beta_5(hK2)+\beta_6(sp1[tPSA])+\beta_7(sp2[tPSA])+\beta_8(sp1[fPSA])+\beta_9(sp2[fPSA])+\beta_{10}(\text{priorbx}) \tag{9}$$

In the equations above "priorbx" is a binary value indicate of whether a subject had a prior biopsy to detect prostate cancer. A value of 1 indicates that a prior biopsy occurred and a value of 0 indicates that the prior biopsy did not occur.

7. Cubic Splines for all Four Assays

In this model, cubic splines are included for each term. In the example provided below, a cubic spline with four knots is described. It should be appreciated, however, that a cubic spline using any suitable number of knots including, but not limited to, five knots, six knots, seven knots, and eight knots, may alternatively be used. The splines may be determined using the following equation:

$$sp[x]1 = \max([x] - knot1, 0)^3 - \max([x] = knot3, 0)^3 \frac{knot4 - knot1}{knot4 - knot3} + \max([x] - knot4, 0)^3 \frac{knot3 - knot1}{knot4 - knot3} \quad (10)$$

$$sp[x]2 = \max([x] - knot2, 0)^3 - \max([x] - knot3, 0)^3 \frac{knot4 - knot2}{knot4 - knot3} + \max([x] - knot2, 0)^3 \frac{knot3 - knot2}{knot4 - knot3} \quad (11)$$

where knot1 and knot4 are external knots for the cubic spline, and knot2 and knot3 are internal knots for the cubic spline. The external knots may be set as the minimum and maximum levels of tPSA, fPSA, iPSA, or hK2 in a population. An internal knot (e.g., knot2) may be set as the 33.3 percentile value of tPSA, fPSA, iPSA, or hK2 levels in a population. Another internal knot (e.g., knot3) may be set as the 66.6 percentile value of tPSA, fPSA, iPSA, or hK2 levels in a population.

In some embodiments, the internal knots are specified within the range of between about 2 to about 8 and between about 3 to about 6 for tPSA, between about 0.25 to about 2 and between about 0.5 to about 1.5 for fPSA, between about 0.2 to about 0.5 and between about 0.4 to about 0.8 for iPSA, and between about 0.02 to about 0.04 and between about 0.04 to about 0.08 for hK2. For example, in one implementation, values of 3.92 and 5.61 are used for the internal knots for tPSA, values of 0.82 and 1.21 are used for the internal knots for fPSA, values of 0.3 and 0.51 are used for the internal knots of iPSA, and values of 0.036 and 0.056 are used for the internal knots of hK2.

In certain embodiments, one or more internal knots for tPSA may independently be in the range of between about 3 to about 5, between about 3 to about 6, between about 2.5 to about 6, between about 2.5 to about 6.5, between about 5 to about 8, between about 5.5 to about 8, between about 5 to about 9, between about 5 to about 10, between about 1 to about 5, between about 1 to about 4, and between about 1 to about 3. Other ranges are also possible.

In certain embodiments, one or more internal knots for fPSA may independently be in the range of between about 0.1 to about 1.0, between about 0.1 to about 1.2, between about 0.3 to about 0.8, between about 0.4 to about 0.9, between about 0.5 to about 1.2, between about 0.7 to about 1.4, between about 0.7 to about 0.9, between about 1.1 to about 1.6, between about 1.1 to about 1.2, and between about 1.1 to about 2. Other ranges are also possible.

In certain embodiments, one or more internal knots for iPSA may independently be in the range of between about 0.05 to about 0.5, between about 0.1 to about 0.5, between about 0.2 to about 0.5, between about 0.1 to about 0.8, between about 0.2 to about 0.8, between about 0.4 to about 0.8, between about 0.4 to about 1.0, between about 0.3 to about 0.6, between about 0.5 to about 1.0, and between about 0.6 to about 0.8. Other ranges are also possible.

In certain embodiments, one or more internal knots for hK2 may independently be in the range of between about 0.01 to about 0.03, between about 0.01 to about 0.04, between about 0.01 to about 0.05, between about 0.02 to about 0.05, between about 0.02 to about 0.06, between about 0.03 to about 0.05, between about 0.4 to about 0.07, between about 0.04 to about 1.0, between about 0.5 to about 1.0, and between about 0.6 to about 1.0. Other ranges are also possible.

As discussed above, cubic splines incorporating any suitable number of internal knots (e.g., three, four, five, six internal knots) may be used, and the example of a cubic spline including two internal knots is provided merely for illustration and not limitation. In embodiments that include more than two internal knots, the knots may be placed within one or more of the ranges discussed above, or in some other suitable range. For example, in some embodiments, the knots may be specified such that the length of the segments of the spline between each of the pairs of neighboring knots is essentially equal.

The model may be represented as:

$$L = \beta_0 + \beta_1(\text{Age}) + \beta_2(tPSA) + \beta_3(fPSA) + \quad (12)$$
$$\beta_4(iPSA) + \beta_5(hK2) + \beta_6(sp1[tPSA]) + \beta_7(sp2[tPSA]) +$$
$$\beta_8(sp1[fPSA]) + \beta_9(sp2[fPSA]) + \beta_{10}(sp1[iPSA]) +$$
$$\beta_{11}(sp2[iPSA]) + \beta_{12}(sp1[hK2]) + \beta_{13}(sp2[hK2]) + \beta_{14}(priorbx)$$

8. tPSA Threshold Model

In some embodiments, the model selected may depend on the whether or not a threshold level of tPSA is detected in sample. In some embodiments, if the level of tPSA is above a threshold in a sample, then the predictive model is as follows:

$$L = \beta_0 + \beta_1(tPSA) + \beta_2(DRE)_{neg} + \beta_3(DRE)_{pos} + \beta_4(priorbx) \quad (13)$$

In some embodiments, the range of values of the weighting coefficients in this model are as set forth in Table 1 below. Coefficients suitable for determining the probability that a prostate tissue biopsy will have a cancer of any grade are shown in the second and third columns; whereas coefficients suitable for determining the probability that a prostate tissue biopsy will have a cancer of high grade are shown in the fourth and fifth columns.

TABLE 1

Weighting Coefficients to be used when level of tPSA is greater than Threshold

| Weighting Coefficient | Cancer of Any Grade | | Cancer of High Grade (Gleason Score >=7.0) | |
|---|---|---|---|---|
| Ranges | Low | High | Low | High |
| $\beta_0$ | −1.22E+00 | −9.07E−01 | 7.83E−01 | 9.31E−01 |
| $\beta_1$ | 1.04E−01 | 1.22E−01 | 1.24E−02 | 1.59E−02 |
| $\beta_2$ | −6.62E−02 | −4.99E−02 | −2.19E−01 | −1.72E−01 |
| $\beta_3$ | 1.34E−01 | 1.71E−01 | 5.23E−01 | 6.44E−01 |
| $\beta_4$ | −1.30E+00 | −8.91E−01 | −1.94E+00 | −1.68E+00 |

In some embodiments, if the level of tPSA detected in a sample is less than or equal to a threshold level, then the predictive model is as follows:

$$L = \beta_3 + \beta_1(\text{Age}) + \beta_2(tPSA) + \beta_3 sp1(tPSA) + \beta_4 sp2(tPSA) + \qquad (14)$$

$$\beta_5(fPSA) + \beta_6 sp1(fPSA) + \beta_7 sp2(fPSA) + \beta_8(iPSA) +$$

$$\beta_9(hK2) + \beta_{10}(DRE_{neg}) + \beta_{11}(DRE_{pos}) + \beta_{12}(priorbx)$$

In some embodiments, the range of values of the weighting coefficients in this model are as set forth in Table 2 below. Coefficients suitable for determining the probability that a prostate tissue biopsy will have a cancer of any grade are shown in the second and third columns; whereas coefficients suitable for determining the probability that a prostate tissue biopsy will have a cancer of high grade are shown in the fourth and fifth columns.

TABLE 2

Weighting Coefficients to be used when level of tPSA is less than or equal to a threshold

| Weighting Coefficient | Cancer of Any Grade | | Cancer of High Grade (Gleason Score >7.0) | |
|---|---|---|---|---|
| Ranges | Low | High | Low | High |
| $\beta_0$ | −2.86E+00 | −1.97E+00 | −7.35E+00 | −6.00E+00 |
| $\beta_1$ | 2.88E−01 | 4.03E−01 | 4.79E−02 | 6.38E−02 |
| $\beta_2$ | 3.76E−01 | 4.72E−01 | 7.44E−01 | 9.19E−01 |
| $\beta_3$ | −2.18E−04 | −1.78E−04 | −6.43E−03 | −4.32E−03 |
| $\beta_4$ | −1.22E−03 | −9.46E−04 | 1.20E−02 | 1.66E−02 |
| $\beta_5$ | −3.63E+00 | −3.18E+00 | −6.27E+00 | −4.43E+00 |
| $\beta_6$ | 5.07E−01 | 7.07E−01 | 7.63E−01 | 1.04E+00 |
| $\beta_7$ | −2.02E+00 | −1.55E+00 | −2.76E+00 | −2.17E+00 |
| $\beta_8$ | 4.16E−02 | 5.45E−02 | 1.96E+00 | 2.40E+00 |
| $\beta_9$ | 7.87E+00 | 1.11E+01 | 6.62E+00 | 7.59E+00 |
| $\beta_{10}$ | −6.62E−02 | −4.65E−02 | −2.44E−01 | −1.74E−01 |
| $\beta_{11}$ | 1.28E−01 | 1.85E−01 | 4.57E−01 | 5.89E−01 |
| $\beta_{12}$ | −1.45E+00 | −1.01E+00 | −1.97E+00 | −1.53E+00 |

The spline terms of sp1(tPSA), sp2(tPSA), sp1(fPSA), and sp2(fPSA) in the model above may be determined according to the cubic spline formula presented above under model #7 above (Equations (10) and (11)). In some embodiments, the values of internal knots 2 and 3 and external knots 1 and 4 are within the ranges set forth in Table 3 below for tPSA and fPSA.

TABLE 3

| Knot value ranges | | | | |
|---|---|---|---|---|
| Knot value | Total PSA | | Free PSA | |
| ranges | Low | High | Low | High |
| Knot 1 | 0 | 2 | 0 | 0.5 |
| Knot 2 | 3.72E+00 | 4.16E+00 | 7.38E−01 | 9.43E−01 |
| Knot 3 | 4.71E+00 | 6.56E+00 | 1.10E+00 | 1.43E+00 |
| Knot 4 | 2.33E+02 | 3.13E+02 | 2.04E+01 | 2.78E+01 |

Computer Implementation

Figure 1B:
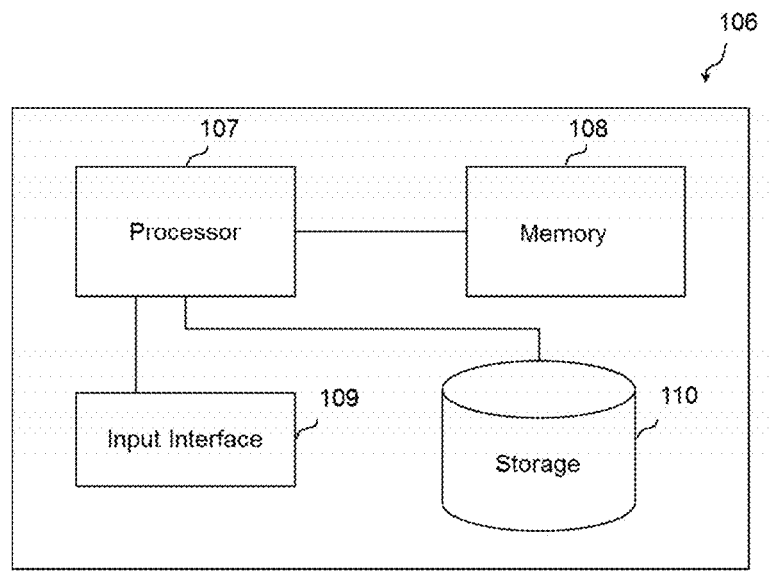
FIG. 1B is a non-limiting schematic of a computer configured for implementing a process for determining the probability that a biopsy will contain detectable prostate cancer (e.g., a detectable aggressive prostate cancer)

An illustrative implementation of a computer system 106 on which some or all of the techniques and/or user interactions described herein may be implemented is shown in FIG. 1B. The computer system 106 may include one or more processors 107 and one or more computer-readable non-transitory storage media (e.g., memory 108 and one or more non-volatile storage media 110). The processor(s) 107 may control writing data to and reading data from the memory 108 and the non-volatile storage device 110 in any suitable manner, as the aspects of the present invention described herein are not limited in this respect.

To perform any of the functionality described herein, the processor(s) 107 may execute one or more instructions, such as program modules, stored in one or more computer-readable storage media (e.g., the memory 108), which may serve as non-transitory computer-readable storage media storing instructions for execution by the processor 107. Generally, program modules include routines, programs, objects, components, data structures, etc. that perform particular tasks or implement particular abstract data types. Embodiments may also be implemented in distributed computing environments where tasks are performed by remote processing devices that are linked through a communications network. In a distributed computing environment, program modules may be located in both local and remote computer storage media including memory storage devices. Data inputs and program commands may be received by the computer 106 through a input interface 109. The input interface 109 may comprise a keyboard, touchscreen, USB port, CD drive, DVD drive, or other input interface.

Computer 106 may operate in a networked environment using logical connections to one or more remote computers. The one or more remote computers may include a personal computer, a server, a router, a network PC, a peer device or other common network node, and typically include many or all of the elements described above relative to the computer 106. Logical connections between computer 106 and the one or more remote computers may include, but are not limited to, a local area network (LAN) and a wide area network (WAN), but may also include other networks. Such networks may be based on any suitable technology and may operate according to any suitable protocol and may include wireless networks, wired networks or fiber optic networks. Such networking environments are commonplace in offices, enterprise-wide computer networks, intranets and the Internet.

When used in a LAN networking environment, the computer 106 may be connected to the LAN through a network interface or adapter. When used in a WAN networking environment, the computer 106 typically includes a modem or other means for establishing communications over the WAN, such as the Internet. In a networked environment, program modules, or portions thereof, may be stored in the remote memory storage device.

Various inputs described herein for assessing a risk of prostate cancer and/or determining a prostate gland volume may be received by computer 106 via a network (e.g., a LAN, a WAN, or some other network) from one or more remote computers or devices that stores data associated with the inputs. One or more of the remote computers/devices may perform analysis on remotely-stored data prior to sending analysis results as the input data to computer 300. Alternatively, the remotely stored data may be sent to computer 106 as it was stored remotely without any remote analysis. Additionally, inputs may be received directly by a user of computer 106 using any of a number of input interfaces (e.g., input interface 109) that may be incorporated as components of computer 106.

Various outputs described herein, including output of a probability of prostate cancer risk and/or prostate gland volume, may be provided visually on an output device (e.g., a display) connected directly to computer 106 or the output(s) may be provided to a remotely-located output device connected to computer 106 via one or more wired or wireless networks, as embodiments of the invention are not limited in this respect. Outputs described herein may additionally or alternatively be provided other than using visual presentation. For example, computer 300 or a remote computer to which an output is provided may include one or more output interfaces including, but not limited to speakers, and vibratory output interfaces, for providing an indication of the output.

Figure 1C:
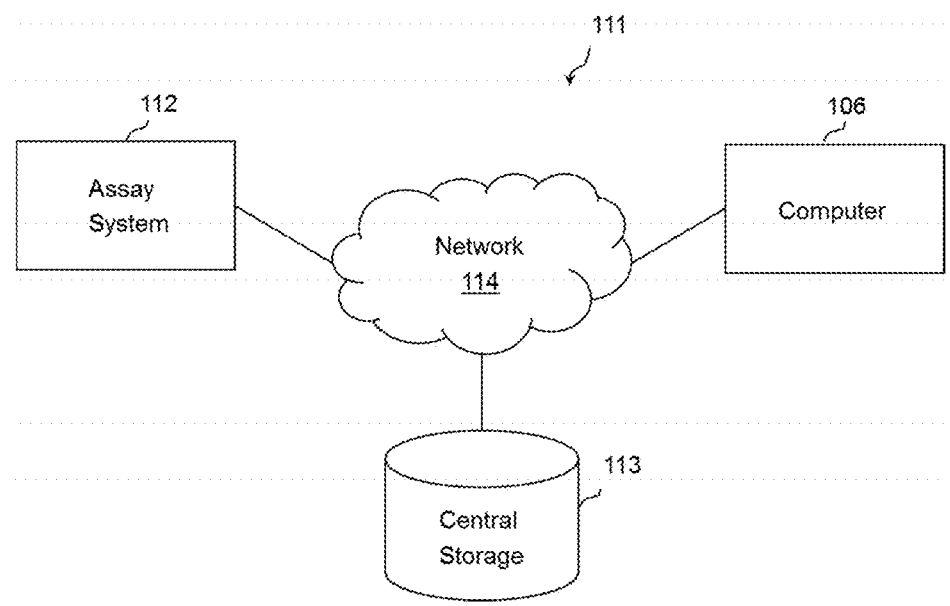
FIG. 1C is a non-limiting schematic of a computer network configured for implementing a process for determining the probability that a biopsy will contain detectable prostate cancer (e.g., a detectable aggressive prostate cancer)

It should be appreciated that although computer 106 is illustrated in FIG. 1 as being a single device, in some embodiments, computer 106 may comprise a plurality of devices communicatively coupled to perform some or all of the functionality described herein, and computer 106 is only one illustrative implementation of a computer that may be used in accordance with embodiments of the invention. For example, in some embodiments, computer 106 may be integrated into and/or in electronic communication with the system. As described above, in some embodiments, computer 106 may be included in a networked environment, where information about one or more blood markers, used to determine a probability of prostate cancer and/or prostate gland volume, is sent from an external source to computer 106 for analysis using one or more of the techniques described herein. An illustrative networked environment 111 in accordance with some embodiments of the invention is shown in FIG. 1C. In networked environment 111, computer 106 is connected to an assay system 112 via network 114. As discussed above, network 114 may be any suitable type of wired or wireless network, and may include one or more local area networks (LANs) or wide area networks (WANs), such as the Internet.

The calculation methods, steps, simulations, algorithms, systems, and system elements described herein may be implemented using a computer system, such as the various embodiments of computer systems described below. The methods, steps, systems, and system elements described herein are not limited in their implementation to any specific computer system described herein, as many other different machines may be used.

The computer system may include a processor, for example, a commercially available processor such as one of the series x86, Celeron and Pentium processors, available from Intel, similar devices from AMD and Cyrix, the 680X0 series microprocessors available from Motorola, the PowerPC microprocessor from IBM, and ARM processors. Many other processors are available, and the computer system is not limited to a particular processor.

A processor typically executes a program called an operating system, of which Windows 7, Windows 8, UNIX, Linux, DOS, VMS, MacOS and OSX, and iOS are examples, which controls the execution of other computer programs and provides scheduling, debugging, input/output control, accounting, compilation, storage assignment, data management and memory management, communication control and related services. The processor and operating system together define a computer platform for which application programs in high-level programming languages are written. The computer system is not limited to a particular computer platform.

The computer system may include a memory system, which typically includes a computer readable and writeable non-volatile recording medium, of which a magnetic disk, optical disk, a flash memory and tape are examples. Such a recording medium may be removable, for example, a floppy disk, read/write CD or memory stick, or may be permanent, for example, a hard drive.

Such a recording medium stores signals, typically in binary form (i.e., a form interpreted as a sequence of one and zeros). A disk (e.g., magnetic or optical) has a number of tracks, on which such signals may be stored, typically in binary form, i.e., a form interpreted as a sequence of ones and zeros. Such signals may define a software program, e.g., an application program, to be executed by the microprocessor, or information to be processed by the application program.

The memory system of the computer system also may include an integrated circuit memory element, which typically is a volatile, random access memory such as a dynamic random access memory (DRAM) or static memory (SRAM). Typically, in operation, the processor causes programs and data to be read from the non-volatile recording medium into the integrated circuit memory element, which typically allows for faster access to the program instructions and data by the processor than does the non-volatile recording medium.

The processor generally manipulates the data within the integrated circuit memory element in accordance with the program instructions and then copies the manipulated data to the non-volatile recording medium after processing is completed. A variety of mechanisms are known for managing data movement between the non-volatile recording medium and the integrated circuit memory element, and the computer system that implements the methods, steps, systems and system elements described above is not limited thereto. The computer system is not limited to a particular memory system.

At least part of such a memory system described above may be used to store one or more data structures (e.g., look-up tables) or equations described above. For example, at least part of the non-volatile recording medium may store at least part of a database that includes one or more of such data structures. Such a database may be any of a variety of types of databases, for example, a file system including one or more flat-file data structures where data is organized into data units separated by delimiters, a relational database where data is organized into data units stored in tables, an object-oriented database where data is organized into data units stored as objects, another type of database, or any combination thereof.

The computer system may include a video and audio data I/O subsystem. An audio portion of the subsystem may include an analog-to-digital (A/D) converter, which receives analog audio information and converts it to digital information. The digital information may be compressed using known compression systems for storage on the hard disk to use at another time. A typical video portion of the I/O subsystem may include a video image compressor/decompressor of which many are known in the art. Such compressor/decompressors convert analog video information into compressed digital information, and vice-versa. The compressed digital information may be stored on hard disk for use at a later time.

The computer system may include one or more output devices. Example output devices include a cathode ray tube (CRT) display, liquid crystal displays (LCD) and other video output devices, printers, communication devices such as a modem or network interface, storage devices such as disk or tape, and audio output devices such as a speaker.

The computer system also may include one or more input devices. Example input devices include a keyboard, keypad, track ball, mouse, pen and tablet, communication devices such as described above, and data input devices such as audio and video capture devices and sensors. The computer system is not limited to the particular input or output devices described herein.

It should be appreciated that one or more of any type of computer system may be used to implement various embodiments described herein. Aspects of the disclosure may be implemented in software, hardware or firmware, or any combination thereof. The computer system may include specially programmed, special purpose hardware, for example, an application-specific integrated circuit (ASIC). Such special-purpose hardware may be configured to implement one or more of the methods, steps, simulations, algorithms, systems, and system elements described above as part of the computer system described above or as an independent component.

The computer system and components thereof may be programmable using any of a variety of one or more suitable computer programming languages. Such languages may include procedural programming languages, for example, C, Pascal, Fortran and BASIC, object-oriented languages, for example, C++, Java and Eiffel and other languages, such as a scripting language or even assembly language.

The methods, steps, simulations, algorithms, systems, and system elements may be implemented using any of a variety of suitable programming languages, including procedural programming languages, object-oriented programming languages, other languages and combinations thereof, which may be executed by such a computer system. Such methods, steps, simulations, algorithms, systems, and system elements can be implemented as separate modules of a computer program, or can be implemented individually as separate computer programs. Such modules and programs can be executed on separate computers.

Such methods, steps, simulations, algorithms, systems, and system elements, either individually or in combination, may be implemented as a computer program product tangibly embodied as computer-readable signals on a computer-readable medium, for example, a non-volatile recording medium, an integrated circuit memory element, or a combination thereof. For each such method, step, simulation, algorithm, system, or system element, such a computer program product may comprise computer-readable signals tangibly embodied on the computer-readable medium that define instructions, for example, as part of one or more programs, that, as a result of being executed by a computer, instruct the computer to perform the method, step, simulation, algorithm, system, or system element.

It should be appreciated that various embodiments may be formed with one or more of the above-described features. The above aspects and features may be employed in any suitable combination as the present invention is not limited in this respect. It should also be appreciated that the drawings illustrate various components and features which may be incorporated into various embodiments. For simplification, some of the drawings may illustrate more than one optional feature or component. However, the invention is not limited to the specific embodiments disclosed in the drawings. It should be recognized that the disclosure encompasses embodiments which may include only a portion of the components illustrated in any one drawing figure, and/or may also encompass embodiments combining components illustrated in multiple different drawing figures.

The embodiments and methods described herein may be combined with one or more embodiments and/or methods described in U.S. application Ser. No. 14/671,355, filed on Mar. 27, 2015 and entitled "Compositions and Methods Related to Diagnosis of Prostate Cancer", which is hereby incorporated by reference in its entirety for all purposes.

EXAMPLES

Example 1—Assay and Predictive Model

Described herein is an assay based on a panel of four kallikrein markers that include total prostate specific antigen (tPSA), free PSA (fPSA), intact PSA (iPSA), and human Kallikrein 2 (hK2) linked to patient specific information via a multivariate algorithm. This algorithm returns two calibrated probabilities: one for the risk of cancer of any grade and another for the risk of high grade cancer (Gleason 7 or greater) prior to biopsy.

The four kallikrein markers have been studied individually and in various combinations for prostate cancer detection applications. A logistic regression algorithm incorporating the blood plasma levels of these four markers as well as patient-specific information such as age, result from a digital rectal exam (DRE) and existence of prior negative prostate biopsy(-ies) demonstrated a higher positive predictive value for prostate cancer than the PSA test alone.

Levels (e.g., in ng/mL) of tPSA, fPSA, iPSA, and hK2 present in human plasma samples were determined using the AutoDELFIA automatic immunoassay system. The averaged amount of each marker was calculated from the duplicate tests for each marker and used in a predictive model to determine a risk score for a given human plasma sample as presented in Example 2. tPSA and fPSA may also be determined using an Elecsys immunoassay analyzer (Roche Diagnostics).

Each run used at least one set of three plates—one plate for f/tPSA, one plate for iPSA and one plate for hK2. A complete run at full capacity involved two sets of these three plates. The whole procedure involved approximately 3 to 5 hours from the initiation to obtaining the test results depending on the number of plates being run.

Three hundred patients were included in an initial calibration study as subset of which had prior negative biopsies. This included the first 5 patients enrolled at each study site, then sequentially enrolled patients. Exclusions were made for samples that were not optimally stored and/or shipped, or where the sample produced abnormal results during measurement of the kallikrein markers.

Logistic Regression Algorithm for Calculating Risk of Cancer on Biopsy

A formula for a predictive model for calculating risk of cancer on biopsy was established through the calibration study and is presented below. As noted, a different formula is used depending on the total PSA levels. Moreover, different weighting coefficients are used depending on whether the model is being used to determine the probability of a biopsy containing a detectable cancer of any grade versus a detectable cancer of high grade (e.g., Gleason score of 7.0 or greater). Weighting coefficients are within the ranges specified in Tables 1 and 2 herein. The variables of the formulae are described in Table 4.

If Total PSA >25 ng/mL $$X\beta = \beta_0 + \beta_1 tspa + \beta_2 dre_{neg} + \beta_3 dre_{pos} + \beta_4 priorbx \quad (13)$$

If Total PSA ≤25 ng/mL $$X\beta = \beta_0 + \beta_1 age + \beta_2 tpsa + \beta_3 sptpsa1 + \quad (14)$$
$$\beta_4 sptpsa2 + \beta_5 fpsa + \beta_6 spfpsa1 + \beta_7 spfpsa2 + \beta_8 ipsa +$$
$$\beta_9 hK2 + \beta_9 hK2 + \beta_{10} dre_{neg} + \beta_{11} dre_{pos} + \beta_{12} priorbx$$

$$\text{Risk of Cancer on Biopsy} = \frac{e^{X\beta}}{1 + e^{X\beta}} \quad (15)$$

Restricted Cubic Spline Terms:

For some variables in the models (total PSA and free PSA), restricted cubic spline terms were included, meaning that two additional terms are added to each of the models for each splined term. The formulas for calculating the two spline terms are below.

$$sp[var]1 = \max([var] - knot1, 0)^3 - \max([var] - knot3, 0)^3 \frac{knot4 - knot1}{knot4 - knot3} + \max([var] - knot4, 0)^3 \frac{knot3 - knot1}{knot4 - knot3} \quad [10]$$

$$sp[var]2 = \max([var] - knot2, 0)^3 - \max([var] - knot3, 0)^3 \frac{knot4 - knot2}{knot4 - knot3} + \max([var] - knot4, 0)^3 \frac{knot3 - knot2}{knot4 - knot3} \quad [11]$$

Sp[var]1 and sp[var]2 are computed for total and free PSA using the formulae above. The spline term for total PSA was calculated using knot values within the ranges specified in Table 3.

TABLE 4

Variables for formula for calculating risk of cancer on biopsy

| Variable Name | Description |
|---|---|
| age | Age at Blood Draw |
| tpsa | Total PSA in ng/ml |
| fpsa | Free PSA in ng/ml |
| ipsa | Intact PSA in ng/ml |
| hk2 | hK2 in ng/ml |
| sptpsa1 | First spline term for total PSA |
| sptpsa2 | Second spline term for total PSA |
| spfpsa1 | First spline term for free PSA |
| spfpsa2 | Second spline term for free PSA |
| priorbx | Prior Biopsy; 0 if no prior biopsy, 1 if had prior biopsy |
| dreneg | Value is equal to 1 if the DRE has been confirmed as negative, 0 otherwise |
| drepos | Value is equal to 1 if the DRE has been confirmed as positive, 0 otherwise |

Results from the Calibration

The characteristics of patients enrolled in the calibration phase of the study are shown in Table 5.

TABLE 5

Characteristics of patients in the calibration phase

| Characteristic | Negative Biopsy (N = 173) | Positive Biopsy (N = 127) | p-value |
|---|---|---|---|
| Age at Blood Draw, average age in years (25 and 75 percentiles) | 63 (59, 69) | 65 (60, 70) | 0.046 |
| Abnormal DRE, n | 43 (25%) | 39 (31%) | 0.3 |
| Prior Negative Prostate Biopsy, n | 37 (21%) | 15 (12%) | 0.030 |
| Total PSA, ng/mL (25 and 75 percentiles) | 4.5 (3.4, 5.8) | 5.4 (4.3, 7.5) | <0.0001 |
| Free PSA, ng/mL (25 and 75 percentiles) | 0.9 (0.6, 1.2) | 0.7 (0.5, 1.2) | 0.2 |
| Intact PSA, ng/mL (25 and 75 percentiles) | 0.4 (0.3, 0.6) | 0.5 (0.3, 0.7) | 0.4 |
| hK2, ng/mL (25 and 75 percentiles) | 0.1 (0.0, 0.1) | 0.1 (0.1, 0.1) | 0.034 |
| Clinical T Stage | | | |
| T1C | | 57 (45%) | |
| T2A | | 33 (26%) | |
| T2B | | 15 (12%) | |
| T2C | | 21 (17%) | |
| T3A | | 1 (0.8%) | |
| Biopsy Gleason Grade (Detail) | | | |
| 3 + 3 | | 67 (53%) | |
| 3 + 4 | | 31 (24%) | |
| 3 + 5 | | 1 (0.8%) | |
| 4 + 3 | | 14 (11%) | |
| 4 + 4 | | 8 (6.3%) | |
| 4 + 5 | | 3 (2.4%) | |
| 5 + 4 | | 1 (0.8%) | |
| 5 + 5 | | 2 (1.6%) | |

Model Calibration

A model was developed based on a European cohort. Logistic regression recalibration was used with both slope and intercept coefficients to test for miscalibration on an American cohort.

$$\beta_0 + \beta_1 \log\left(\frac{L}{1 - L}\right) \quad (16)$$

If there was evidence that $\beta_0 \neq 0$ or $\beta_1 \neq 1$, this would indicate that it would be useful to recalibrate the model.

Figure 2:
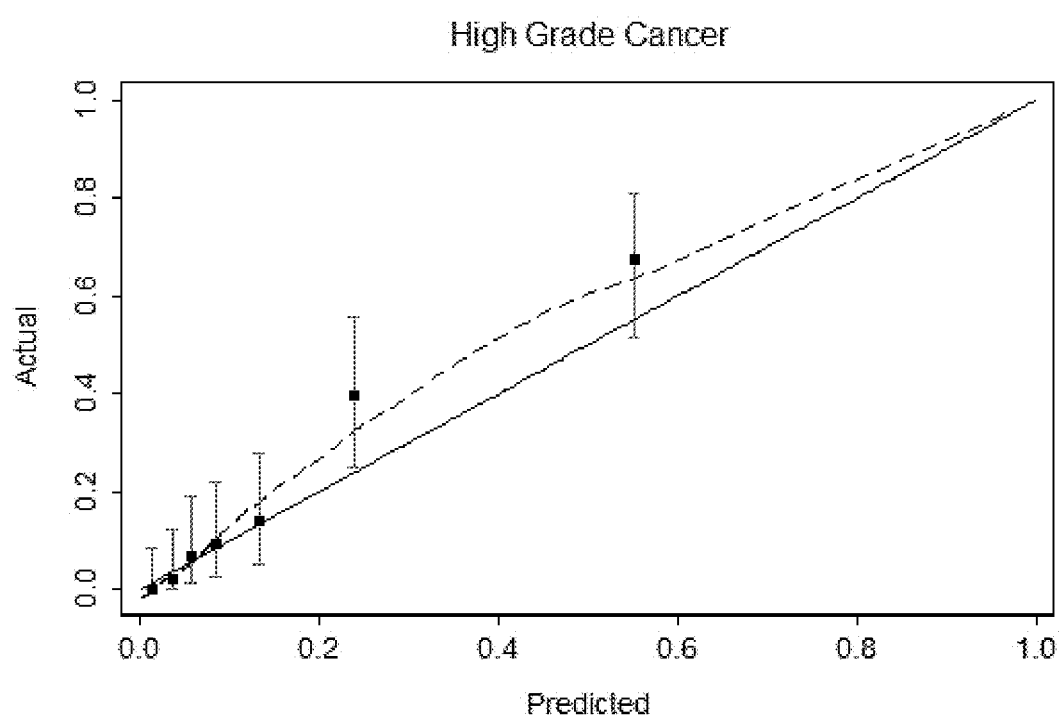
FIG. 2 is a non-limiting example of a graph comparing actual risk versus predicted risk of aggressive prostate cancer (high grade cancer)
Figure 3:
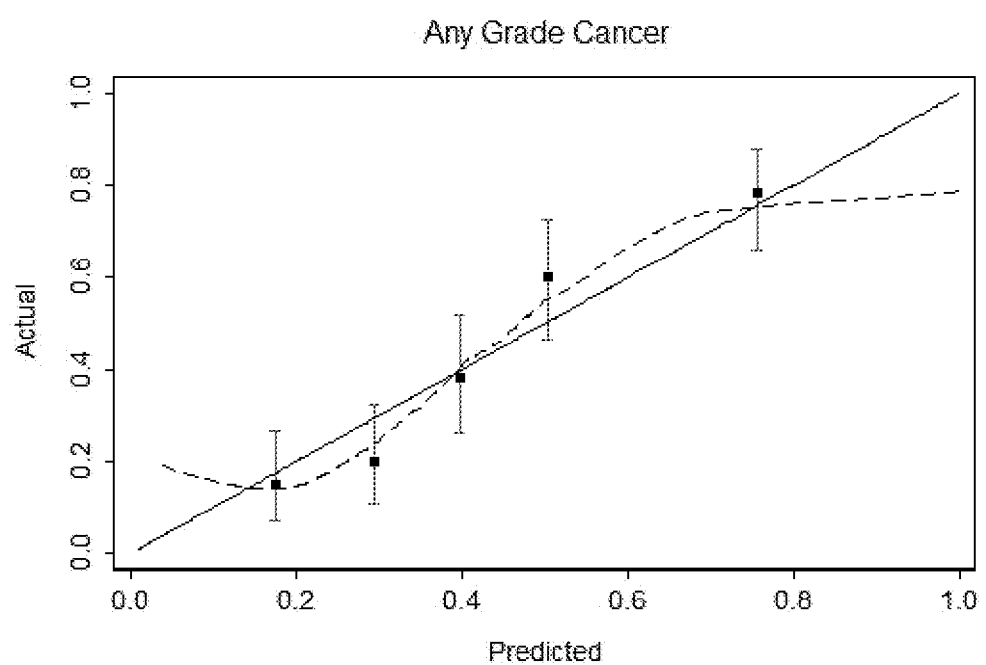
FIG. 3 is a non-limiting example of a graph comparing actual risk versus predicted risk of any grade of cancer.

The model predicting high grade cancer exhibited near perfect calibration for predictions below 0.2 (or 20%), while there appeared to be some underestimation of actual risk for predictions greater than 0.2 (or 20%) (FIG. 2). It is noted that the decision to refer patients for biopsy would occur at thresholds below 0.2 (or 20%), where the model appears to accurately predict the true risk of high grade cancer. For this reason, no recalibration was performed for the high grade model. The model predicting any grade of cancer did not exhibit significant miscalibration, and was therefore not recalibrated (FIG. 3). Data points in FIGS. 2 and 3 shows the relationship between predicted and actual probabilities and the dotted line is a line fitted to the data. Bars indicating the extent of variation in actual probability are shown. The solid line reflects perfect calibration where actual probabilities equal predicted probabilities.

Model Performance

Below is the report of the performance of the predictive model. All statistics were corrected for overfit using repeated 10-fold cross validation.

TABLE 6

Discrimination of the Predictive Model

| | AUC (95% CI) |
|---|---|
| Any Grade Cancer | 0.769 (0.715, 0.824) |
| High Grade Cancer | 0.857 (0.805, 0.909) |

TABLE 7

Brier Score for the Predictive Model

|  | Brier Score |
|---|---|
| Any Grade Cancer | 0.1967 |
| High Grade Cancer | 0.1144 |

Biopsies Avoided Under Varying Biopsy Schemes

The number of High Grade Cancers (Table 5) and Any Grade Cancers (Table 6) found and missed via different biopsying schemes per 1000 patients were determined.

TABLE 8

High Grade Cancers Found/Missed

| Label | Biopsies | Biopsies Avoided | High Grade Cancers Found | High Grade Cancers Missed |
|---|---|---|---|---|
| Prob of High Grade PCa >5% | 686 | 314 | 190 | 10 |
| >7.5% | 538 | 462 | 181 | 19 |
| >10% | 445 | 555 | 173 | 27 |
| >12.5% | 370 | 630 | 167 | 33 |

TABLE 9

Any Grade Cancers Found/Missed

| Label | Biopsies | Biopsies Avoided | Cancers Found | Cancers Missed |
|---|---|---|---|---|
| Prob of High Grade PCa >5% | 686 | 314 | 371 | 52 |
| >7.5% | 538 | 462 | 329 | 95 |
| >10% | 445 | 555 | 297 | 126 |
| >12.5% | 370 | 630 | 270 | 154 |

Decision Curve Analysis

Figure 4:
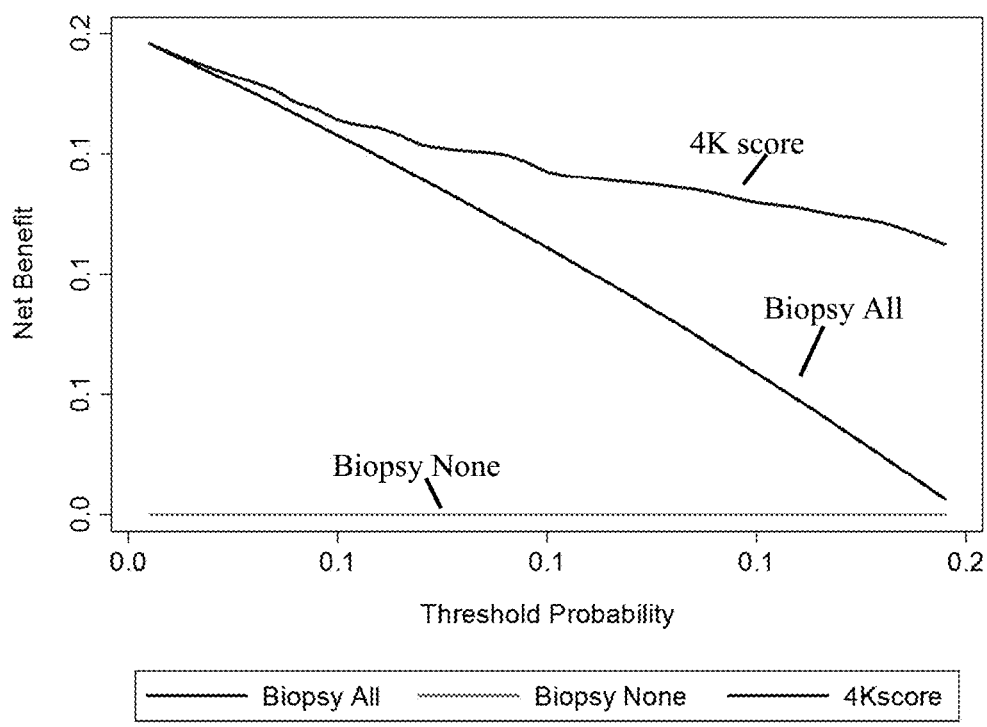
FIG. 4 is a non-limiting example of a graph showing a decision curve analysis for aggressive prostate cancer (high grade cancer)
Figure 5:
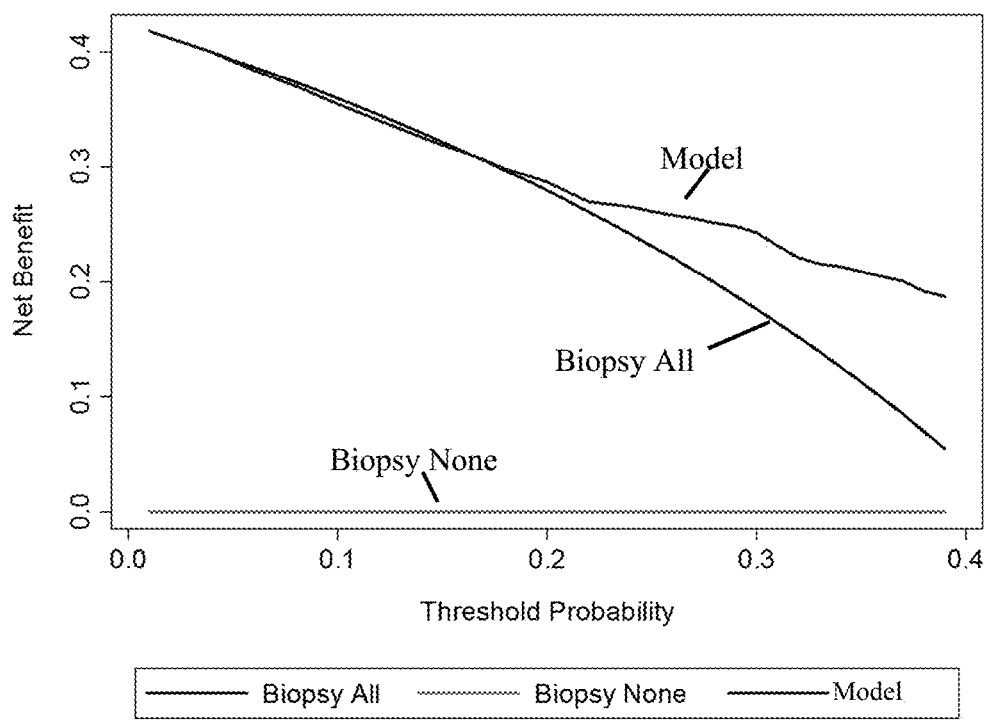
FIG. 5 is a non-limiting example of a graph showing a decision curve analysis for any grade cancer.

The decision curve analysis for High Grade Cancer is shown in FIG. 4. The decision curve analysis for Any Grade Cancer is shown in FIG. 5.

Receiver Operating Curves (ROC)

Figure 6:
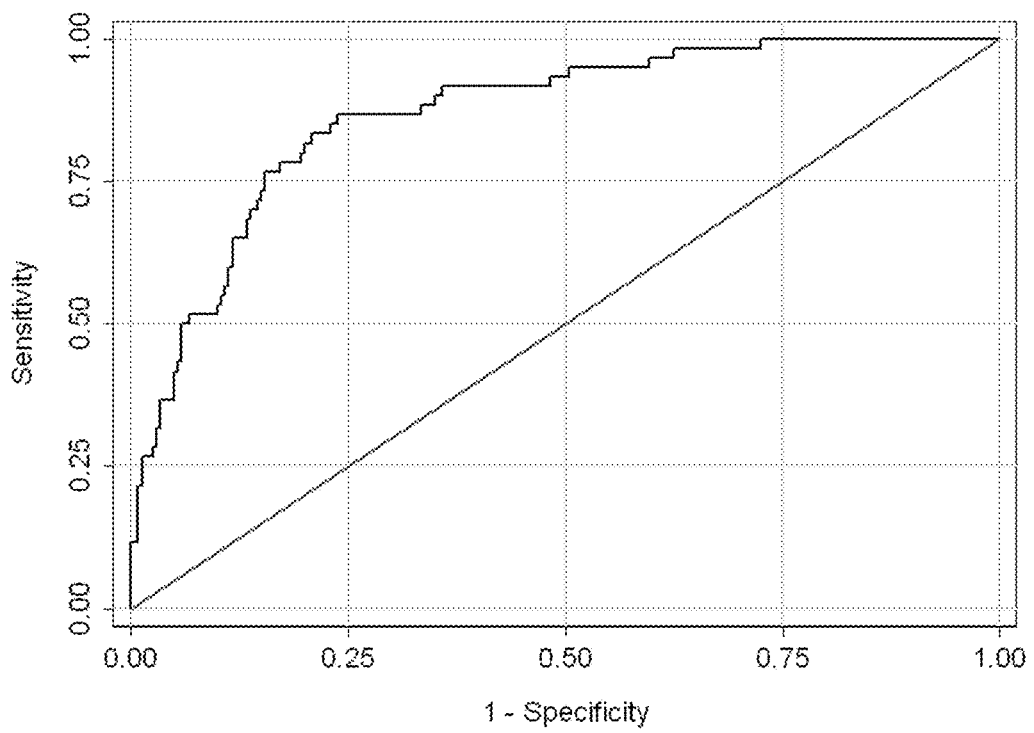
FIG. 6 is a non-limiting example of a graph of a Receiver Operating Curve (ROC) for aggressive prostate cancer (high grade cancer)
Figure 7:
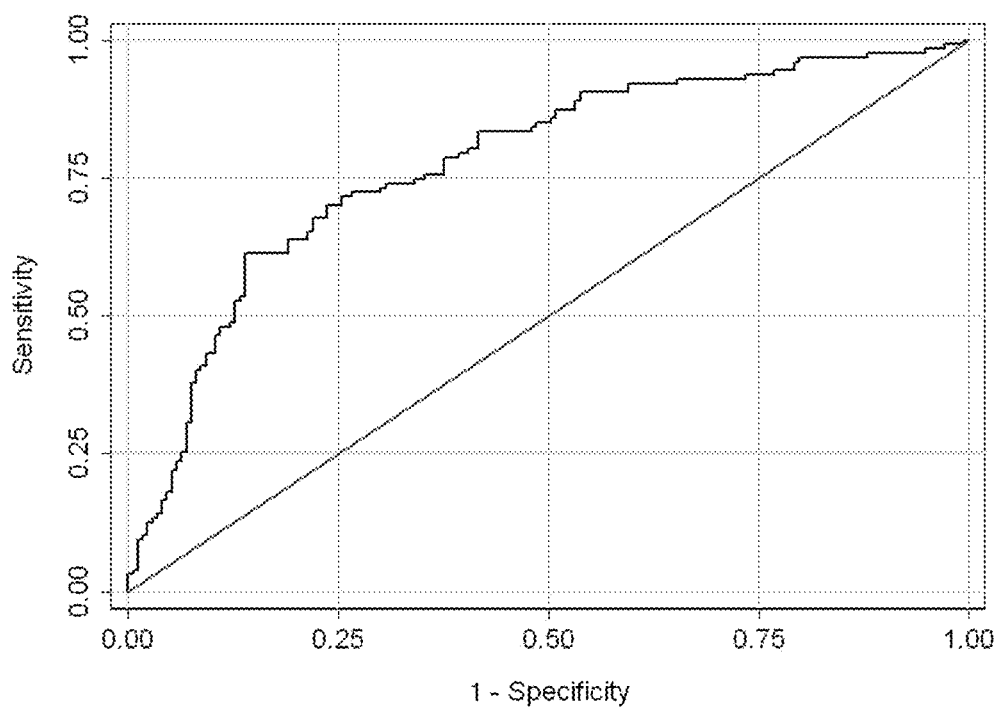
FIG. 7 is a non-limiting example of a graph of a Receiver Operating Curve (ROC) for any grade cancer.

The ROC for High Grade Cancer is shown in FIG. 6. The ROC for Any Grade Cancer is shown in FIG. 7.

Negative Predictive Value and Positive Predictive Value by Biopsy Threshold

Figure 8A:
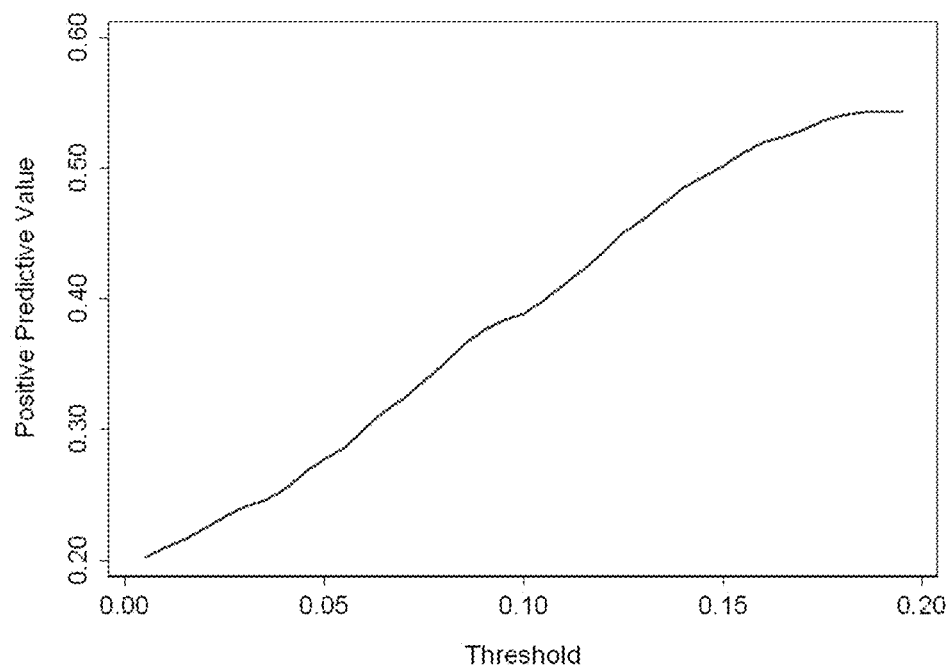
FIG. 8A is a non-limiting example of a graph of a positive predictive value by biopsy threshold for aggressive prostate cancer (high grade cancer)
Figure 8B:
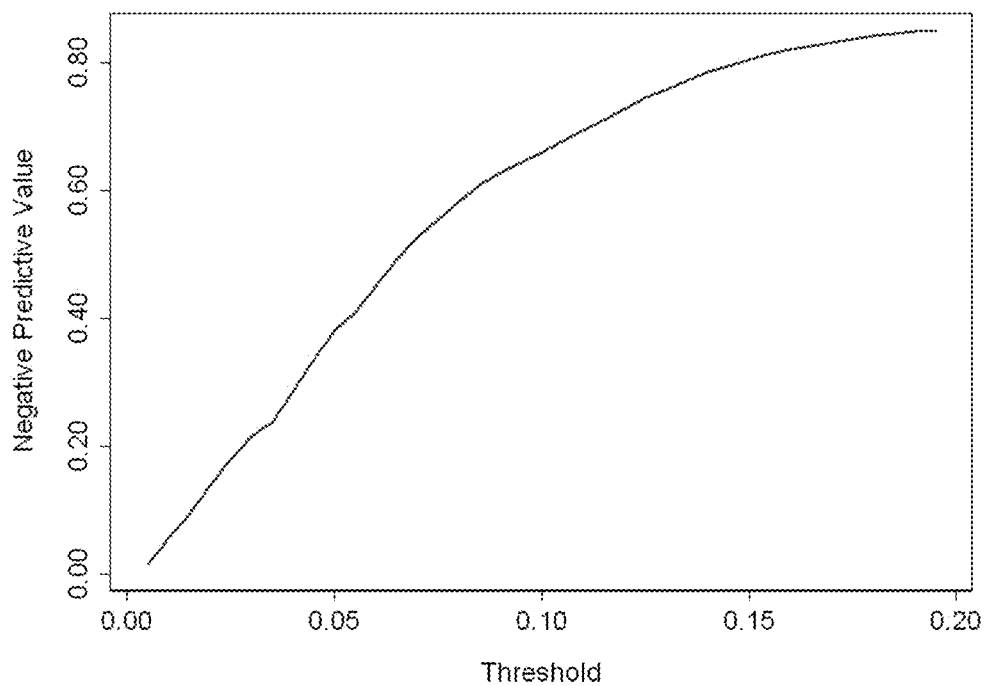
FIG. 8B is a non-limiting example of a graph of a negative predictive value by biopsy threshold for aggressive prostate cancer (high grade cancer)
Figure 9A:
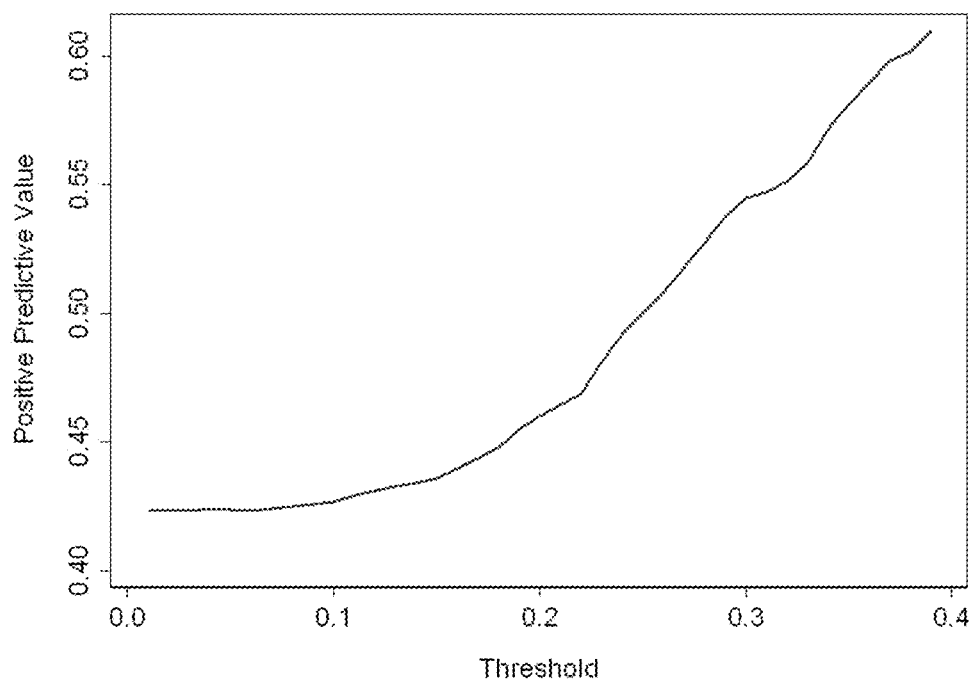
FIG. 9A is a non-limiting example of a graph of a positive predictive value by biopsy threshold for any grade cancer.
Figure 9B:
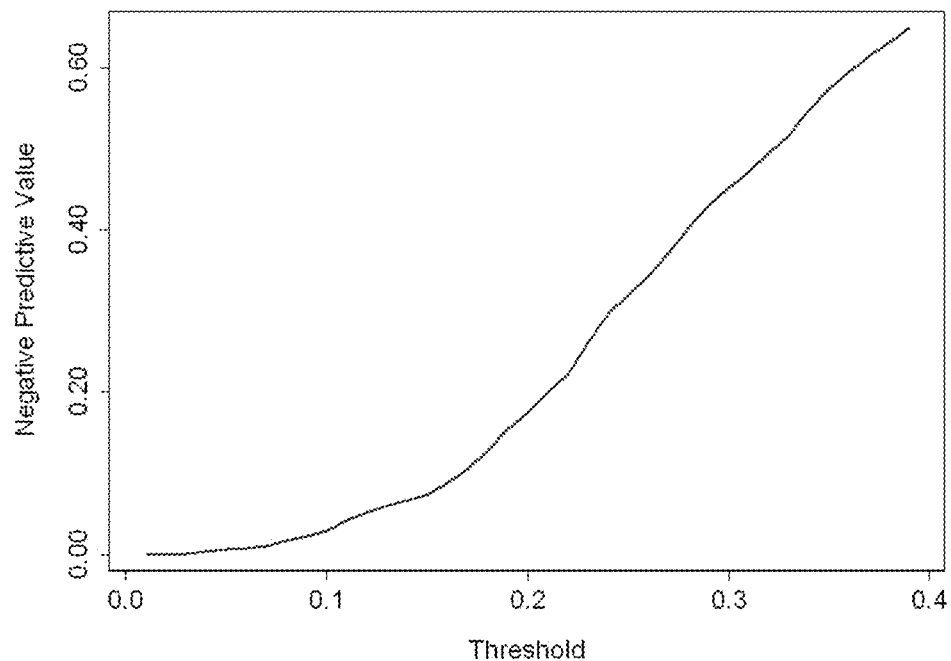
FIG. 9B is a non-limiting example of a graph of a negative predictive value by biopsy threshold for any grade cancer.

The Positive Predictive Value and Negative Predictive Value by Biopsy Threshold for High Grade Cancer are shown in FIGS. 8A and 8B, respectively. The Positive Predictive Value and Negative Predictive Value by Biopsy Threshold for Any Grade Cancer are shown in FIGS. 9A and 9B, respectively.

Example 2: Validation Study

Figure 10:
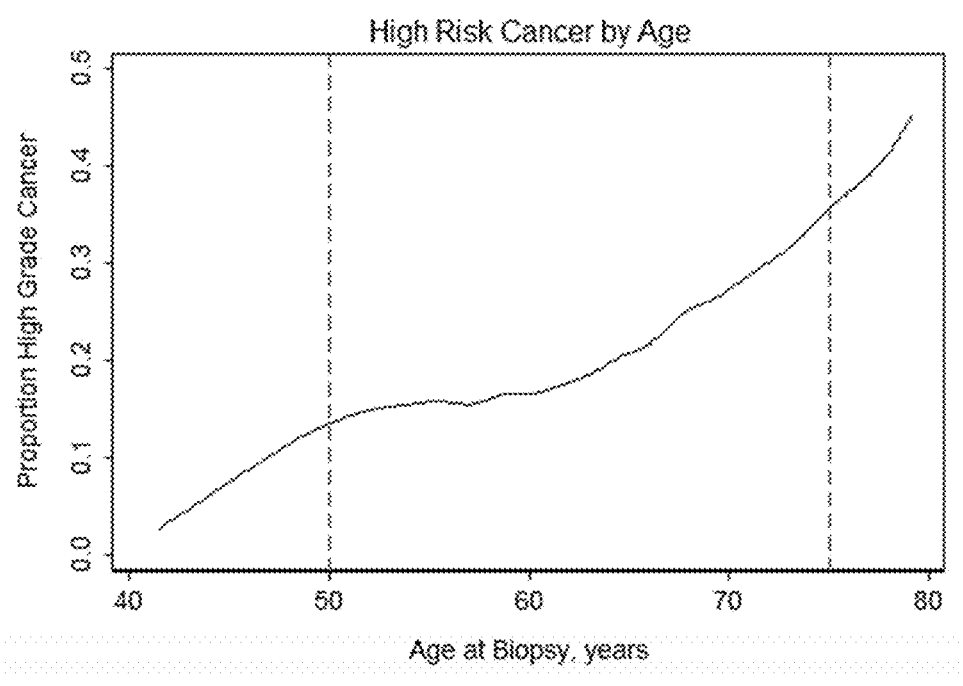
FIG. 10 shows a non-limiting example of a plot showing the proportion of men who harbored aggressive prostate cancer (high grade cancer) by age at biopsy.

An assessment of the performance of the model presented in Example 1 and as set forth in Equations (10, 11, 13, 14), which is referred to in this example as the "test model", was performed based on 663 patients enrolled in the validation phase of the study. Results are presented separately for the entire cohort, men with a prior biopsy, men with no prior biopsy, and men aged 50-75. The FIG. 10 shows the proportion of men who harbored high grade disease by age at biopsy. Older men had much higher rates of high grade disease.

One possibility for the observed increase in risk at higher ages is more selective biopsy. In other words, urologists may only biopsy a man over the age of 70—the upper limit for PSA screening in many guidelines—if there is a compelling reason to do so. To assess whether the increase in is the proportion of high grade cancers among older men was due to biopsy selection we utilized the PCPT risk calculator (See Thompson I M, Ankerst D P, Chi C, Goodman P J, Tangen C M, Lucia M S, Feng Z, Panes H L, Coltman C A Jr. Assessing prostate cancer risk: Results from the Prostate Cancer Prevention Trial, Journal of the National Cancer Institute 98: 529-534, 2006). The PCPT risk calculator was built on a cohort of men where biopsy was offered to all men regardless of age. In a logistic regression model with high grade disease as the outcome and PCPT risk and older age as covariate, if the age coefficient is significant it suggests that the effect of age we are observing is due to the selection, rather than a biologic increase in risk. These results indicate that risk in older men is higher than expected (p=0.072), suggesting a selection effect. A subgroup analysis was performed of men aged 50-75. Since there were 20 patients of an age less than 50, an additional subgroup analysis was conducted that excluded patients aged over 70.

Two separate models were compared: the "test model" and a base model that was based on total PSA, age, prior biopsy, and DRE. Table 10 is an outline of differences in patient characteristics between the calibration phase and the validation phase cohorts.

TABLE 10

Patient Characteristics

| | Validation phase Cohort (N = 663; 69%) | Calibration Phase (N = 300; 31%) | p-value |
|---|---|---|---|
| Age at Blood Draw, years (25 and 75 percentiles) | 64 (58, 69) | 64 (59, 69) | 0.7 |
| <50 | 24 (3.6%) | 19 (6.3%) | |
| 50-75 | 587 (89%) | 261 (87%) | |
| >75 | 52 (7.8%) | 20 (6.7%) | |
| Abnormal DRE | 152 (23%) | 82 (27%) | 0.14 |
| Prior Prostate Biopsy | 128 (19%) | 52 (17%) | 0.5 |
| Total PSA, ng/ml (25 and 75 percentiles) | 4.7 (3.3, 6.8) | 4.8 (3.6, 6.5) | 0.4 |
| Free PSA, ng/ml (25 and 75 percentiles) | 0.9 (0.6, 1.4) | 1.0 (0.6, 1.4) | 0.7 |
| Intact PSA, ng/ml (25 and 75 percentiles) | 0.4 (0.3, 0.7) | 0.4 (0.3, 0.6) | 0.7 |
| hK2, ng/ml (25 and 75 percentiles) | 0.1 (0.1, 0.1) | 0.1 (0.0, 0.1) | 0.4 |
| Positive Biopsy | 297 (45%) | 127 (42%) | 0.5 |
| High Grade Cancer | 146 (22%) | 60 (20%) | 0.5 |

Table 11 below provides patient characteristics of the validation phase cohort separated by cancer status.

It was found that the test model has higher discrimination for high grade disease that the base model, with an increase in AUC by about 0.06. This difference is relatively stable across conditions. It is slightly greater for patients with prior biopsy (0.09) and in the diagnostic "grey zone" (0.07-0.09). Differences between base and test models for the endpoint of positive biopsy are smaller, clearly demonstrating the selectivity of the test models for high grade disease.

Tables 14 and 15 below outline the number of high grade found and missed for all patients and those under 70 years of age via different biopsy schemes per 1000 patients. In an analysis of clinical consequences, it was found that using a cut-point of 7.5% reduces the number of biopsies by about 50%. This does lead to missing some high grade cancers, an effect that is reduced when the analysis is restricted to men aged less than 71. Of younger patients with a risk <7.5%, 5.5% had Gleason score 7 or 8, meaning that 18 biopsies would need to be conducted to find one high grade cancer in this group. Of the missed high grade cancers, 53% were 3+4, 40% were 4+3 and 7% 4+4.

TABLE 11

Validation Study Cohort by Cancer Status

|  | No Cancer (N = 366; 55%) | Cancer (N = 297; 45%) | p-value |
|---|---|---|---|
| Age at Blood Draw, years (25 and 75 percentiles) | 63 (58, 68) | 65 (59, 71) | 0.0004 |
| <50 | 19 (5.2%) | 5 (1.7%) |  |
| 50-75 | 324 (89%) | 263 (89%) |  |
| >75 | 23 (6.3%) | 29 (10%) |  |
| Abnormal DRE | 77 (21%) | 75 (25%) | 0.2 |
| Prior Prostate Biopsy | 90 (25%) | 38 (13%) | 0.0001 |
| Total PSA, ng/ml (25 and 75 percentiles) | 4.3 (2.8, 5.8) | 5.3 (4.0, 8.1) | <0.0001 |
| Free PSA, ng/ml (25 and 75 percentiles) | 0.9 (0.6, 1.4) | 1.0 (0.7, 1.4) | 0.085 |
| Intact PSA, ng/ml (25 and 75 percentiles) | 0.4 (0.3, 0.6) | 0.5 (0.3, 0.7) | 0.0003 |
| hK2, ng/ml (25 and 75 percentiles) | 0.1 (0.0, 0.1) | 0.1 (0.1, 0.1) | <0.0001 |
| Clinical T Stage |  |  |  |
| T1A |  | 1 (0.3%) |  |
| T1B |  | 1 (0.3%) |  |
| T1C |  | 194 (65%) |  |
| T2A |  | 53 (18%) |  |
| T2B |  | 22 (7.4%) |  |
| T2C |  | 23 (7.7%) |  |
| T3A |  | 2 (0.7%) |  |
| T4 |  | 1 (0.3%) |  |
| Biopsy Gleason Grade |  |  |  |
| 6 |  | 151 (51%) |  |
| 7 |  | 102 (34%) |  |
| 8 |  | 25 (8.4%) |  |
| 9 |  | 17 (5.7%) |  |
| 10 |  | 2 (0.7%) |  |

TABLE 12

Model Differences

| All Patients | Test model | Base Model (tPSA, Age, DRE, and Prior Biopsy) | PCPT |
|---|---|---|---|
| High Grade Cancer (Bx GGS >6) | 0.824 (0.784, 0.864) | 0.763 (0.719, 0.806) | 0.760 (0.718, 0.802) |
| Positive Biopsy | 0.729 (0.691, 0.768) | 0.704 (0.665, 0.744) | 0.680 (0.639, 0.720) |
| Age 50-75 |  |  |  |
| High Grade Cancer (Bx GGS >6) | 0.816 (0.771, 0.860) | 0.747 (0.699, 0.796) | 0.741 (0.693, 0.788) |
| Positive Biopsy | 0.730 (0.690, 0.771) | 0.694 (0.651, 0.736) | 0.662 (0.619, 0.706) |
| Prior Biopsy |  |  |  |
| High Grade Cancer (Bx GGS >6) | 0.775 (0.654, 0.896) | 0.687 (0.557, 0.817) | 0.671 (0.524, 0.818) |
| Positive Biopsy | 0.702 (0.596, 0.808) | 0.654 (0.548, 0.759) | 0.639 (0.535, 0.743) |
| Biopsy Naive |  |  |  |
| High Grade Cancer (Bx GGS >6) | 0.835 (0.795, 0.875) | 0.766 (0.720, 0.813) | 0.791 (0.749, 0.834) |
| Positive Biopsy | 0.715 (0.672, 0.758) | 0.692 (0.648, 0.737) | 0.684 (0.639, 0.729) |
| Age less than 71 |  |  |  |
| High Grade Cancer (Bx GGS >6) | 0.822 (0.773, 0.870) | 0.757 (0.705, 0.810) | 0.757 (0.707, 0.806) |
| Positive Biopsy | 0.737 (0.694, 0.780) | 0.709 (0.665, 0.753) | 0.684 (0.639, 0.729) |
| PSA 2-10 ng/mL ("Grey zone") |  |  |  |
| High Grade Cancer (Bx GGS >6) | 0.768 (0.708, 0.829) | 0.700 (0.634, 0.766) | 0.677 (0.612, 0.741) |
| Positive Biopsy | 0.707 (0.657, 0.757) | 0.666 (0.614, 0.718) | 0.622 (0.568, 0.675) |

TABLE 13

Brier Score

| All Patients | Test model | Base Model (tPSA, Age, DRE, and Prior Biopsy) | PCPT |
|---|---|---|---|
| High Grade Cancer (Bx GGS >6) | 0.1255 | 0.1432 | 0.1680 |
| Positive Biopsy | 0.2060 | 0.2178 | 0.2577 |
| Age 50-75 |  |  |  |
| High Grade Cancer (Bx GGS >6) | 0.1222 | 0.1410 | 0.1615 |
| Positive Biopsy | 0.2054 | 0.2210 | 0.2609 |
| Prior Biopsy |  |  |  |
| High Grade Cancer (Bx GGS >6) | 0.1111 | 0.1156 | 0.1166 |
| Positive Biopsy | 0.1787 | 0.1921 | 0.2009 |
| Biopsy Naive |  |  |  |
| High Grade Cancer (Bx GGS >6) | 0.1289 | 0.1498 | 0.1802 |
| Positive Biopsy | 0.2126 | 0.2239 | 0.2712 |
| Age less than 71 |  |  |  |
| High Grade Cancer (Bx GGS >6) | 0.1116 | 0.1308 | 0.1471 |
| Positive Biopsy | 0.1990 | 0.2143 | 0.2495 |

All Patients

TABLE 14

High Grade Cancer

| Label | Biopsies | Biopsies Avoided | High Grade Cancers Found | High Grade Cancers Missed |
|---|---|---|---|---|
| Prob of High Grade PCa >2.5% | 805 | 195 | 210 | 11 |
| >5% | 664 | 336 | 204 | 17 |
| >7.5% | 534 | 466 | 193 | 27 |
| >10% | 454 | 546 | 181 | 39 |
| >12.5% | 386 | 614 | 169 | 51 |

Age Less than 71

TABLE 15

| | | | High Grade | High Grade |
| threshold | Biopsies | Biopsies Avoided | Cancers Found | Cancers Missed |
|---|---|---|---|---|
| Prob of High Grade PCa >2.5% | 779 | 221 | 178 | 11 |
| >5% | 624 | 376 | 170 | 19 |
| >7.5% | 490 | 510 | 161 | 28 |
| >10% | 406 | 594 | 151 | 37 |
| >12.5% | 340 | 660 | 140 | 49 |

Figure 11A:
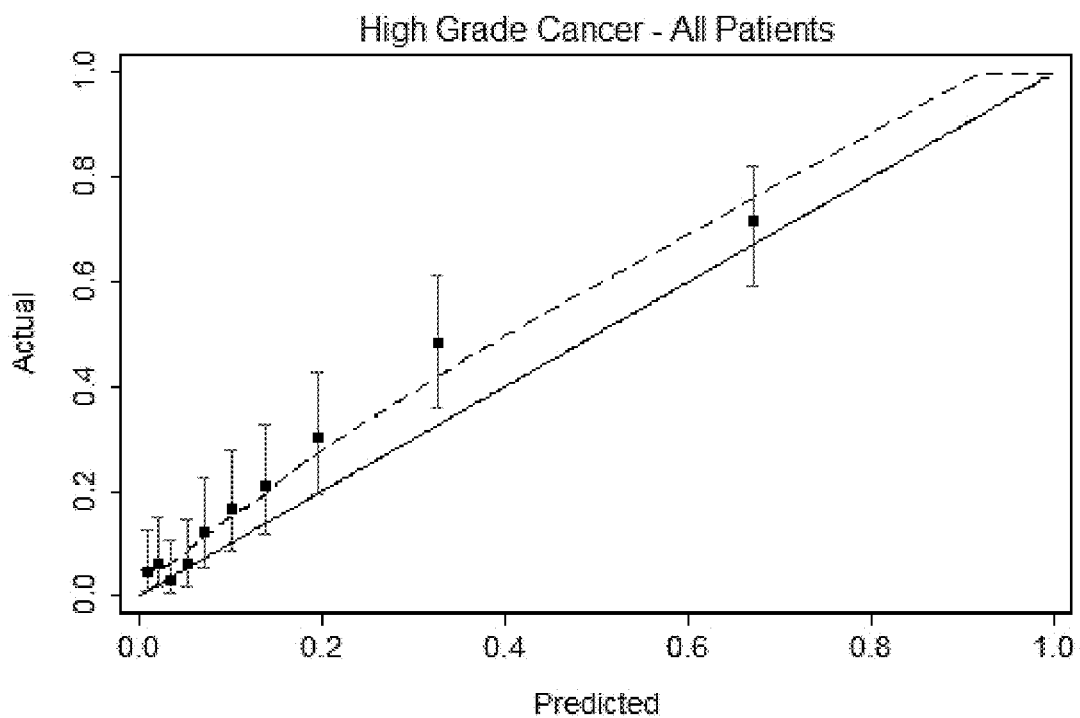
FIGS. 11A and 11B show a non-limiting example of plots showing predicted versus actual probabilities of detecting aggressive prostate cancer (high grade cancer) in all patients of a validation study.
Figure 11B:
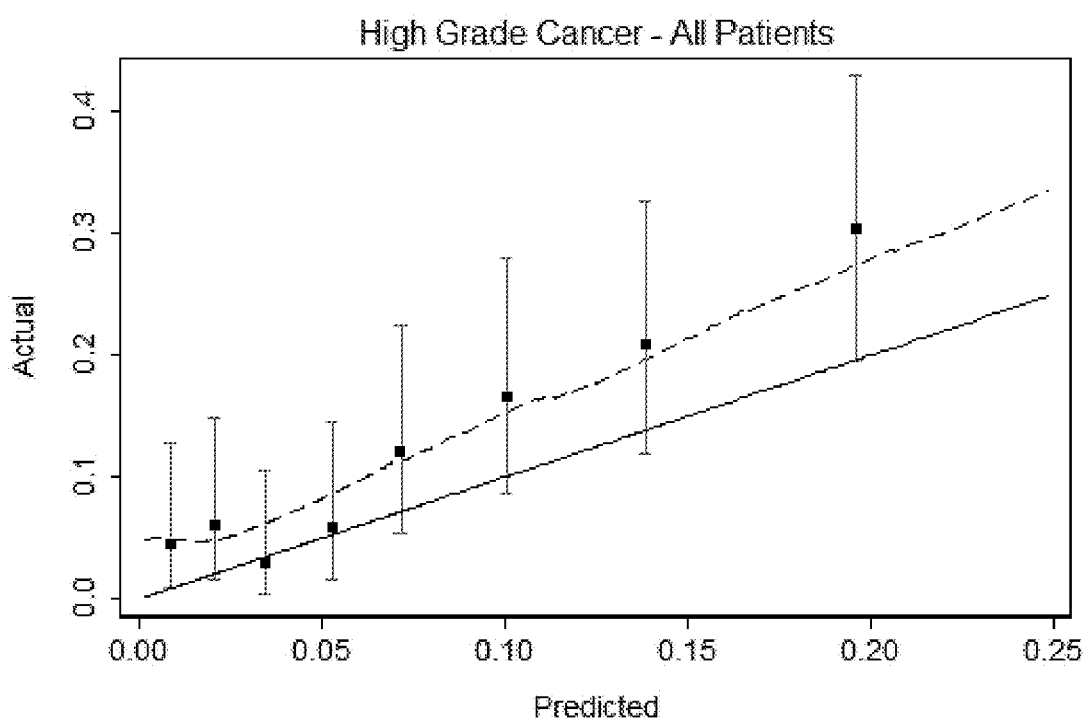
Figure 11C:
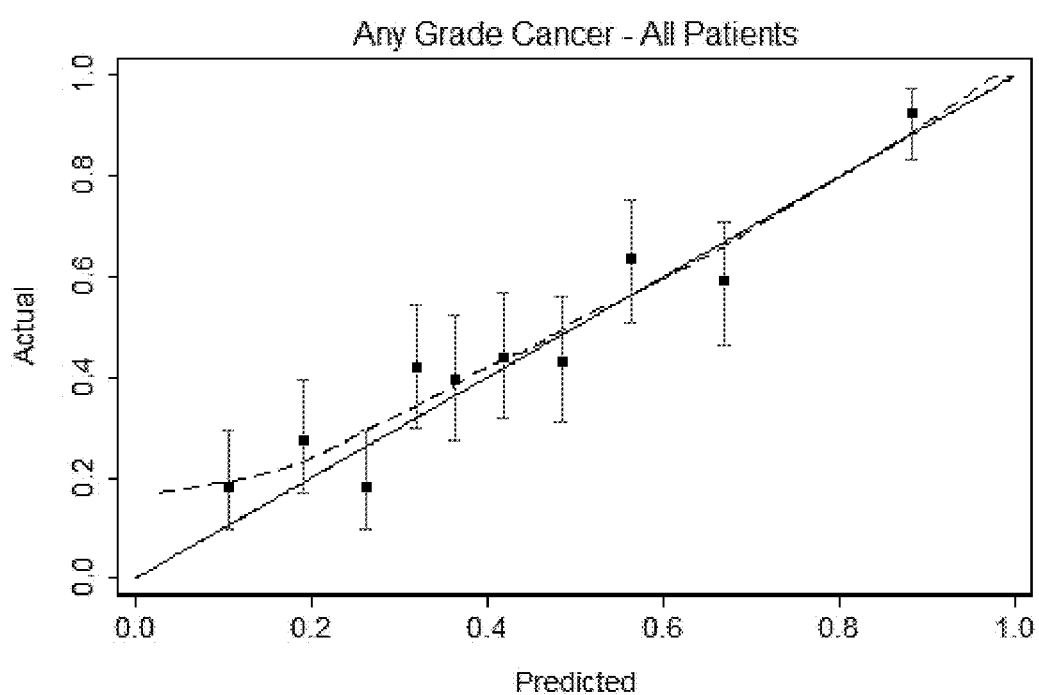
FIG. 11C shows a non-limiting example of a plot showing predicted versus actual probabilities of detecting any grade of cancer in all patients of a validation study.
Figure 12A:
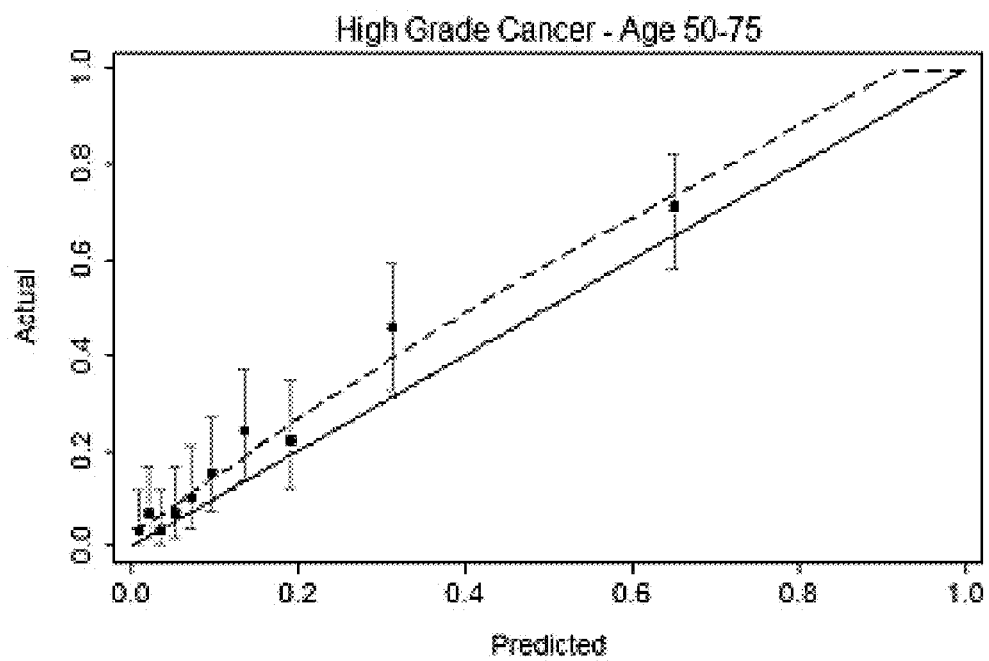
FIGS. 12A and 12B show a non-limiting example of plots showing predicted versus actual probabilities of detecting aggressive prostate cancer (high grade cancer) in patients aged 50-75 of a validation study.
Figure 12B:
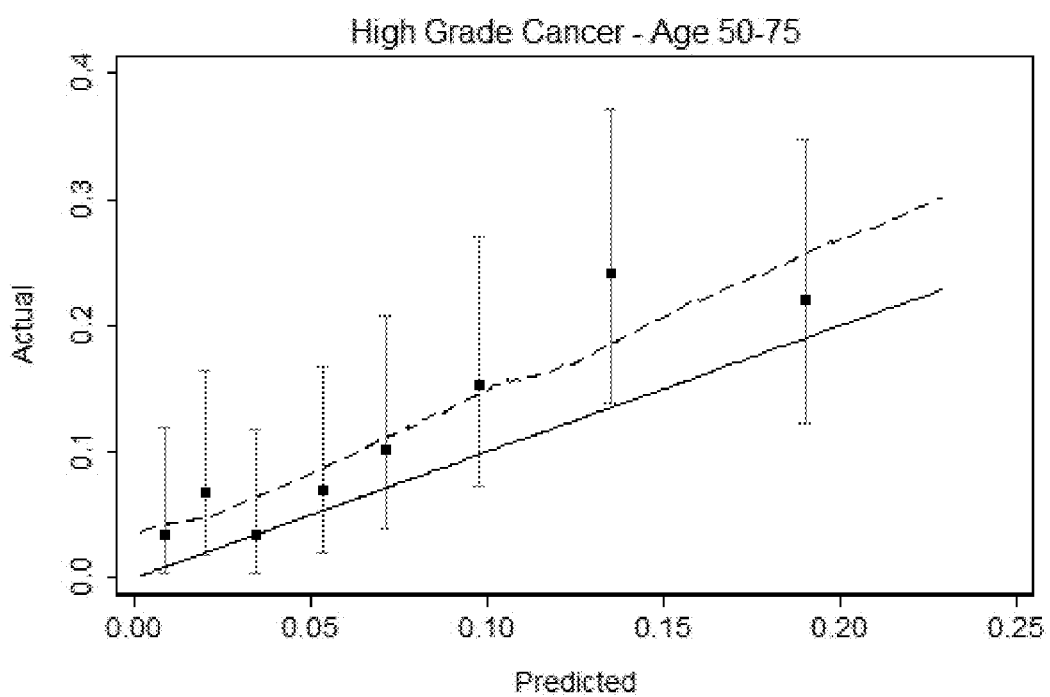
Figure 12C:
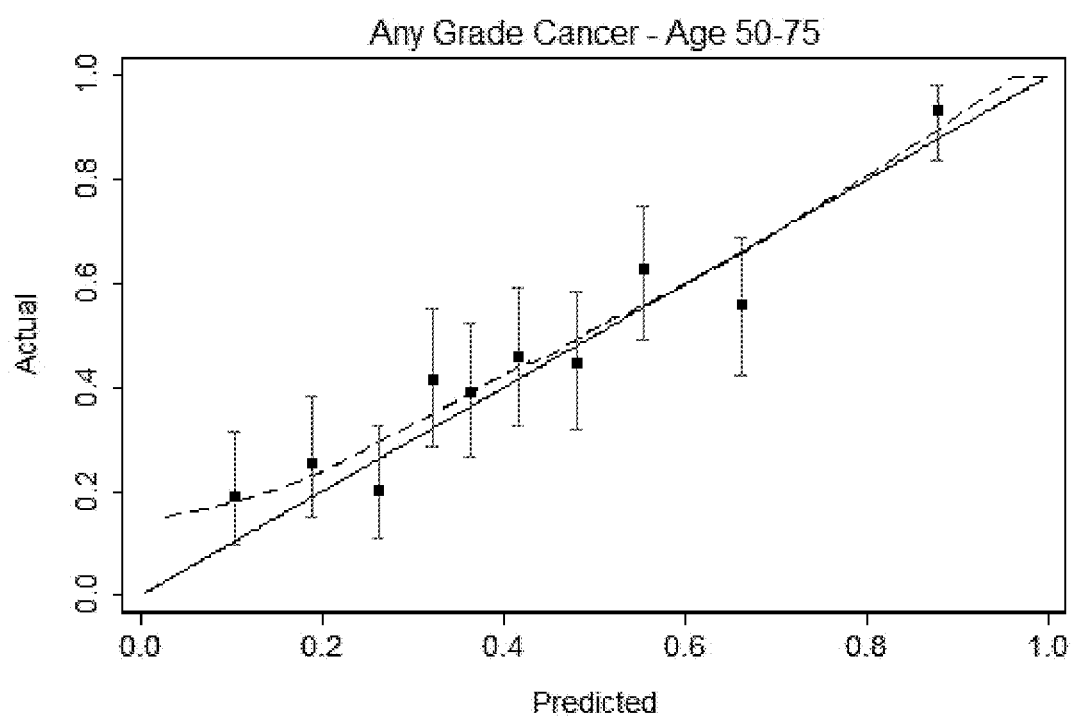
FIG. 12C shows a non-limiting example of a plot showing predicted versus actual probabilities of detecting any grade of cancer in all patients aged 50-75 of a validation study.
Figure 13A:
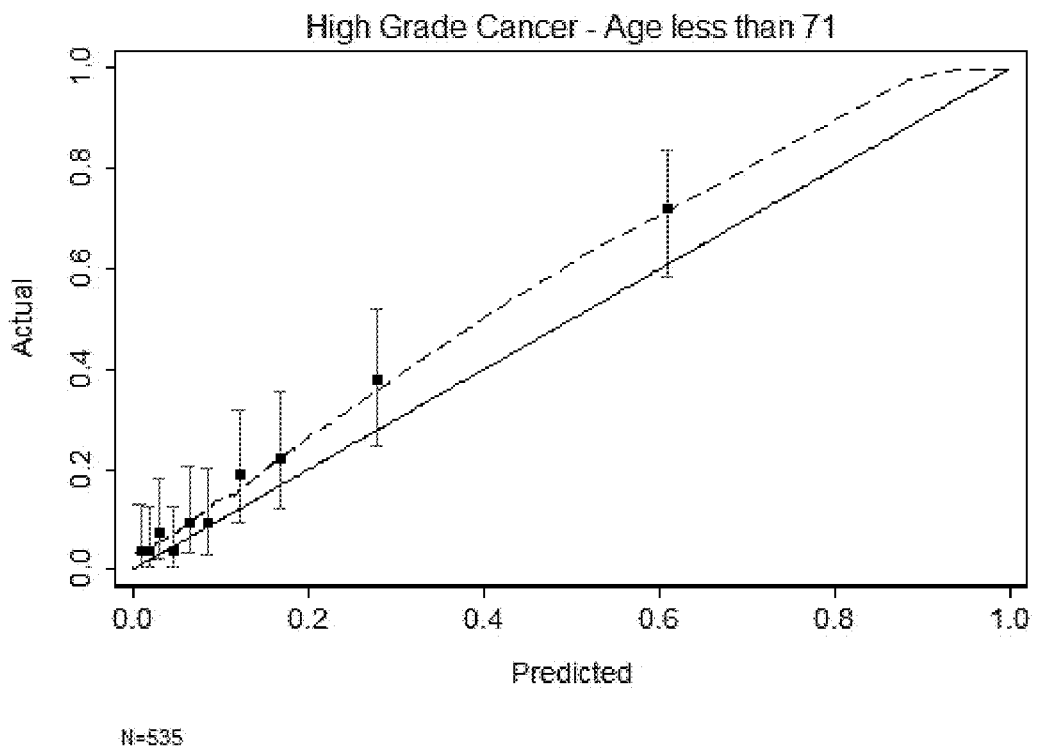
FIGS. 13A and 13B show a non-limiting example of plots showing predicted versus actual probabilities of detecting aggressive prostate cancer (high grade cancer) in patients aged less than 71 of a validation study.
Figure 13B:
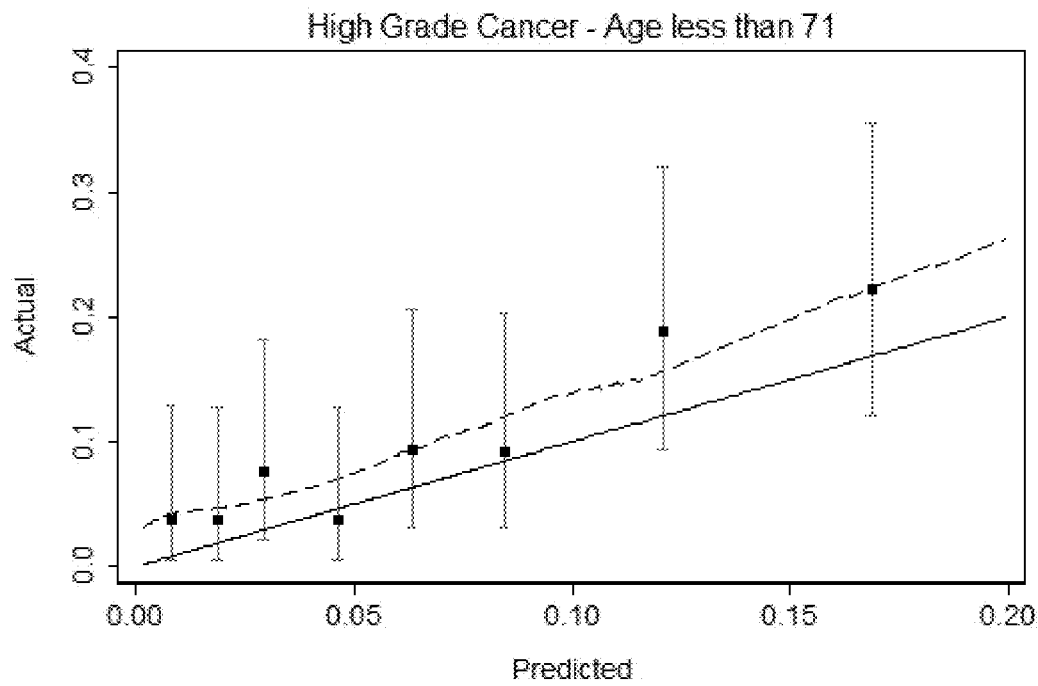
Figure 13C:
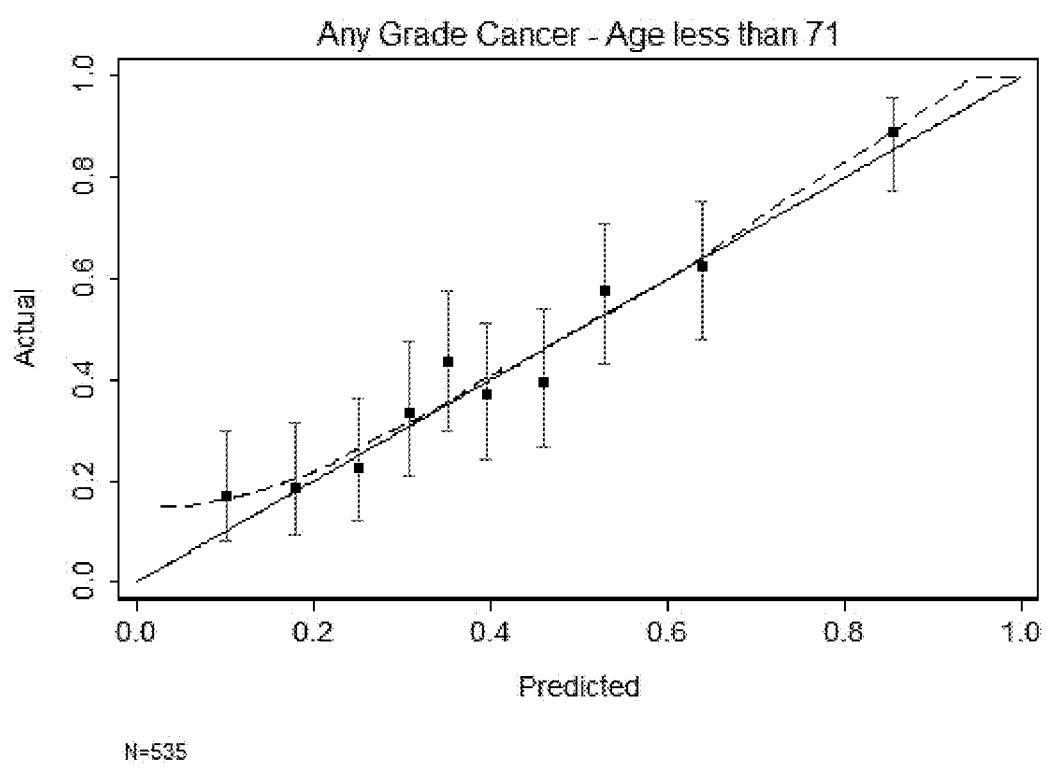
FIG. 13C shows a non-limiting example of a plot showing predicted versus actual probabilities of detecting any grade of prostate cancer in patients aged less than 71 of a validation study.

FIGS. 11A and 11B show predicted versus actual probabilities of detecting high grade cancer in all patients (n=663). FIG. 11C shows predicted versus actual probabilities of detecting any grade cancer in all patients (n=663). FIGS. 12A and 12B show predicted versus actual probabilities of detecting high grade cancer in patients aged 50-75 (n=587). FIG. 12C shows predicted versus actual probabilities of detecting any grade cancer in all patients aged 50-75 (n=587). FIGS. 13A and 13B show predicted versus actual probabilities of detecting high grade cancer in patients aged less than 71 (n=535). FIG. 13C shows predicted versus actual probabilities of detecting any grade cancer in all patients aged less than 71 (n=535). The foregoing results show that there is a degree of underprediction of risk, an effect that is reduced by restricting the sample to patients aged less than 71. For FIGS. 11 to 13, data points show the relationship between predicted and actual probabilities and the dotted line is a line fitted to the data. Bars indicating the extent of variation in actual probabilities are shown. The solid lines reflect perfect calibration where actual probabilities equal predicted probabilities.

Figure 14A:
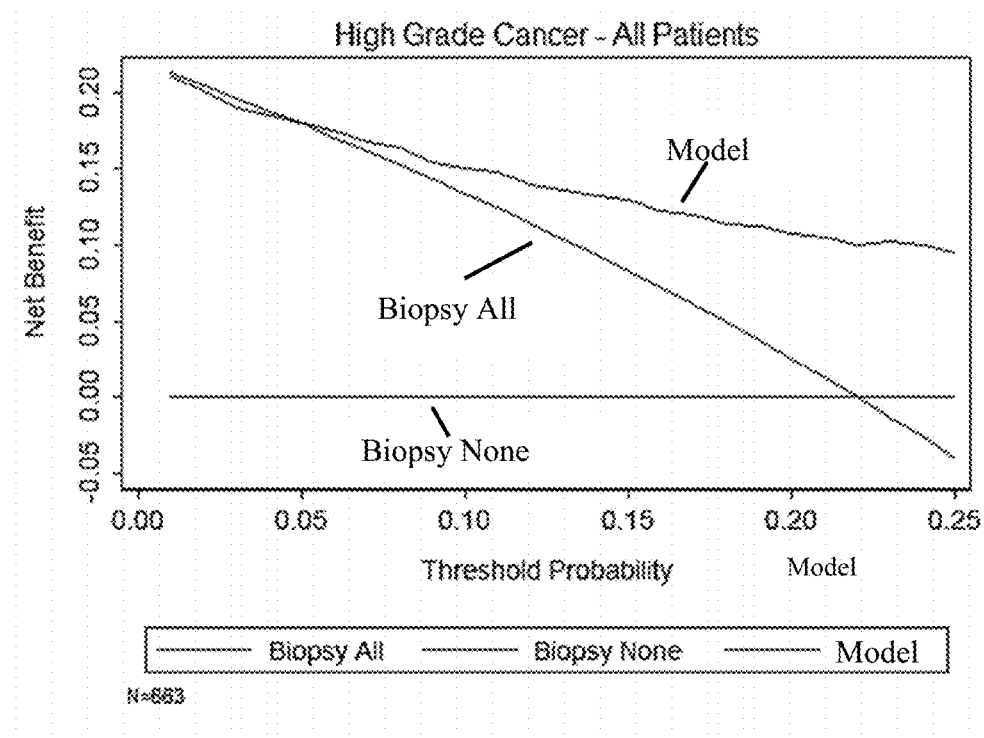
FIGS. 14A and 14B show a non-limiting example of plots showing net benefit versus threshold probability levels for all patients of a validation study.
Figure 14B:
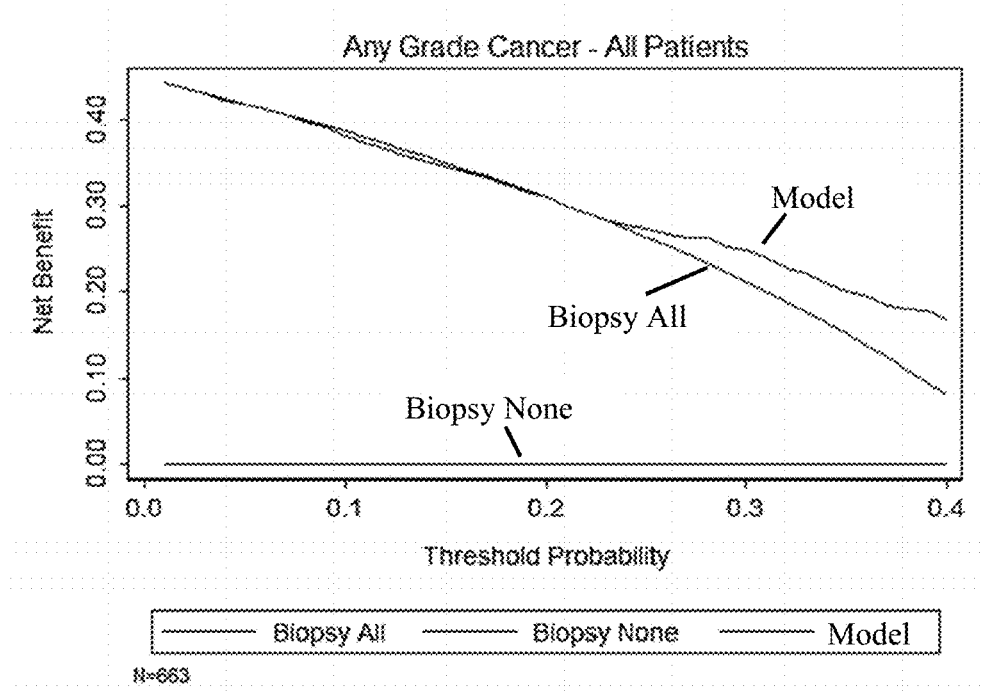
Figure 15A:
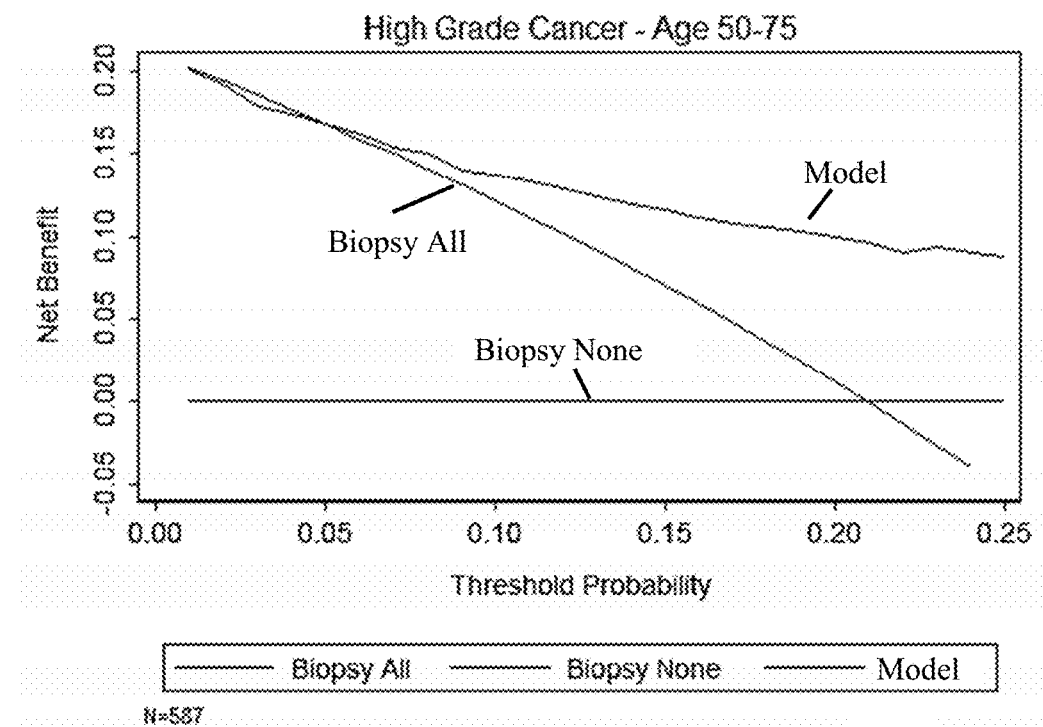
FIGS. 15A and 15B show a non-limiting example of plots showing net benefit versus threshold probability levels for patients aged 50-75 of a validation study.
Figure 15B:
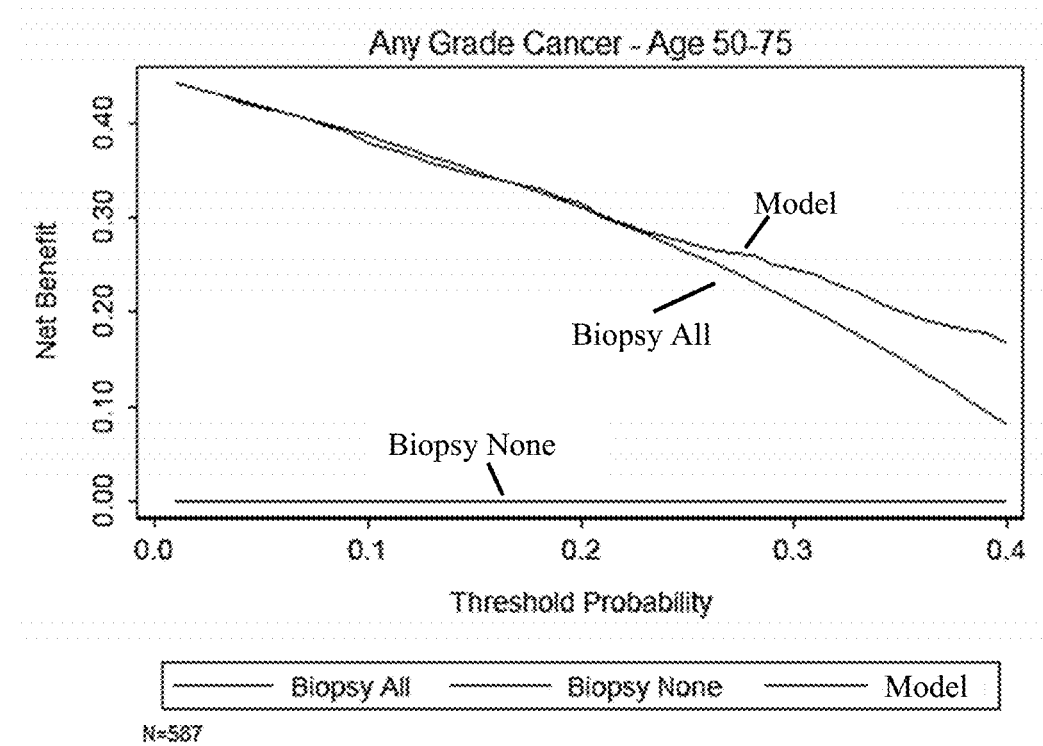
Figure 16A:
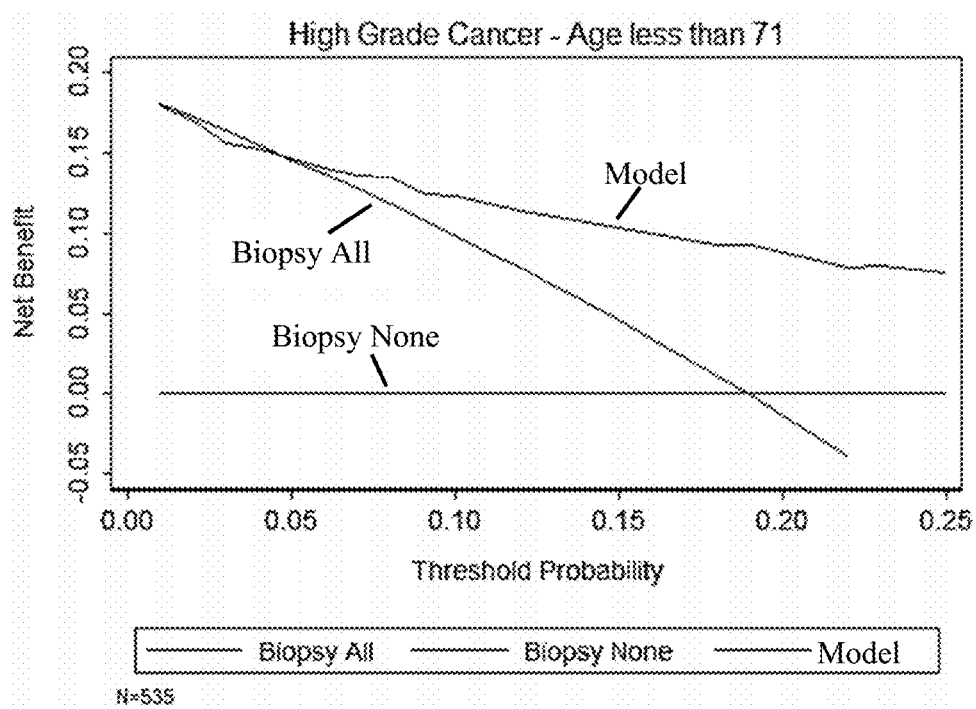
FIGS. 16A and 16B show a non-limiting example of plots showing net benefit versus threshold probability levels for all patients aged less than 71 of a validation study.
Figure 16B:
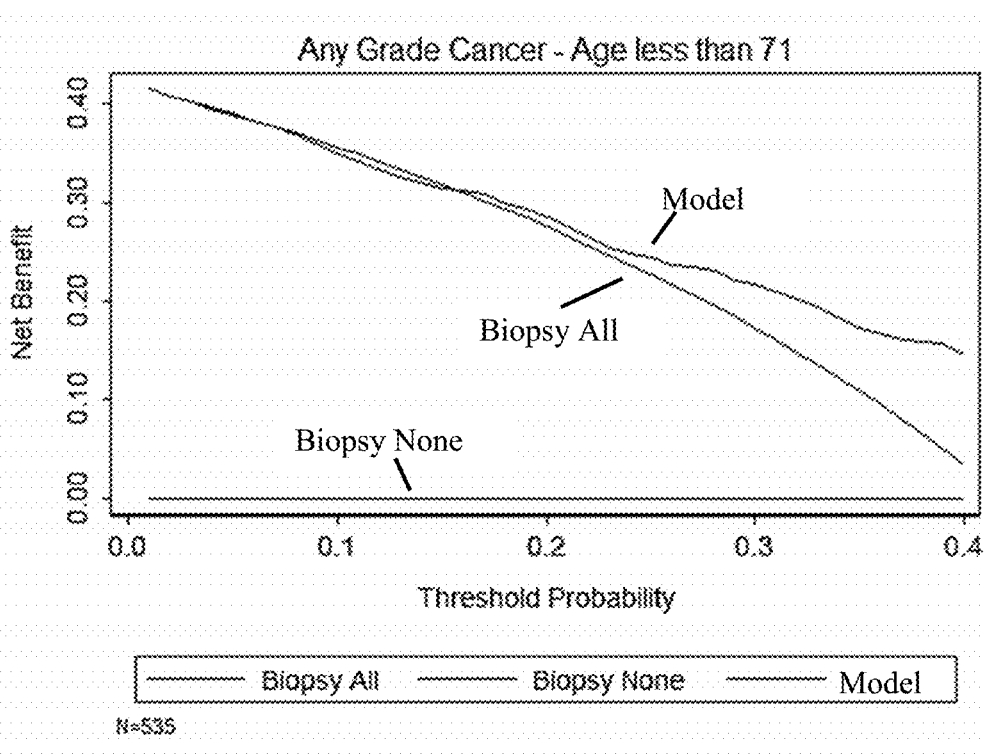

FIGS. 14A and 14B show net benefit versus threshold probability levels for all patients (n=663). FIGS. 15A and 15B show net benefit versus threshold probability levels for patients aged 50-75 (n=587). FIGS. 16A and 16B show net benefit versus threshold probability levels for all patients aged less than 71 (n=535). The data indicate that use of the predictive model is associated with clear net benefit for detecting high grade cancer. This effect is strengthened for the patients aged less than 71. Net benefit is evaluated as described in Vickers A. J. et al., Net benefit and threshold probability were established using methods disclosed in *Med Decis Making*. 2006; 26(6): 565-574, the entire contents of which is incorporated herein by reference.

What is claimed is:

1. A method, comprising:
   i) selecting a subject having a total prostate specific antigen (tPSA) level of less than or equal to 25 ng/ml comprising obtaining a blood sample from the subject, removing blood plasma from the blood sample, and subjecting the blood plasma to an immunoassay that measures a level of tPSA in the blood plasma;
   ii) subjecting the blood plasma from the selected subject to one or more immunoassays that measure levels of kallikrein markers, wherein the kallikrein markers comprise free prostate specific antigen (fPSA), intact prostate specific antigen (iPSA), and human kallikrein 2 (hK2);
   iii) determining the probability that a prostate tissue biopsy obtained from the subject would contain detectable aggressive prostate cancer using a logistic regression model with aggressive prostate cancer as the outcome, wherein the logistic regression model is:

$X\beta = \beta_0 + \beta_1 \text{age} + \beta_2 \text{tpsa} + \beta_3 \text{sptpsa1} + \beta_4 \text{sptpsa2} + \beta_5 \text{fpsa} + \beta_6 \text{spfpsa1} + \beta_7 \text{spfpsa2} + \beta_8 \text{ipsa} + \beta_9 \text{hK2} + \beta_{10} \text{dre}_{neg} + \beta_{11} \text{dre}_{pos} + \beta_{12} \text{priorbx};$ wherein $\beta_0$-$\beta_{12}$ are weighting coefficients, age is the age of the subject when the blood is obtained, tpsa is concentration of tPSA in ng/mL, fpsa is concentration of fPSA in ng/mL, ipsa is concentration of iPSA in ng/mL, hK2 is concentration of hK2 in ng/ml, sptpsa1 is a first spline term for tPSA, sptpsa2 is a second spline term for tPSA, spfpsa1 is a first spline term for fPSA, spfpsa2 is a second spline term for fPSA, $\text{dre}_{neg}$ is a value of 1 if a digital rectal examination has been confirmed as negative or a value of 0 otherwise, $\text{dre}_{pos}$ is a value of 1 if a digital rectal examination has been confirmed as positive or a value of 0 otherwise, and priorbx is 0 if no prior negative biopsy and 1 if the subject had a prior negative biopsy;
   iv) comparing the probability from step iii) to a probability threshold level of 12.5%, wherein when the probability from step iii) is below the probability threshold level of 12.5%, the subject undergoes active surveillance without obtaining a prostate tissue biopsy from the subject, wherein the active surveillance comprises repeating steps i)-iii) at least once within an interval of 6 months to 1 year to calculate a repeated probability; and
   v) obtaining a prostate tissue biopsy from the subject when the probability of step iii) or the repeated probability of step iv) is above the probability threshold level of 12.5%; and
   vi) identifying the subject as having aggressive prostate cancer based on the obtained prostate tissue biopsy of step v) indicating the presence of aggressive prostate cancer and the probability of step iii) or the repeated probability of step iv) being above the probability threshold level of 12.5%, wherein the aggressive prostate cancer is associated with a Gleason score of 7 or more; and
   vii) treating the identified subject of step vi), wherein treatment comprises prostatectomy or radiotherapy.

2. The method of claim 1 further comprising repeating steps i)-iii) at least twice in step iv), wherein the interval between each set of steps i)-iii) is in a range of 6 months to 1 year.

3. The method of claim 1 further comprising repeating steps i)-iii) at least once per year for up to five years before step v).

* * * * *